(12) United States Patent
Jennings et al.

(10) Patent No.: US 9,579,459 B2
(45) Date of Patent: Feb. 28, 2017

(54) AUTO-INJECTOR

(75) Inventors: Douglas Jennings, Herts (GB); Thomas Kemp, Hertfordshire (GB); Matthew Ekman, Cheshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 841 days.

(21) Appl. No.: 13/994,888

(22) PCT Filed: Dec. 21, 2011

(86) PCT No.: PCT/EP2011/073513
§ 371 (c)(1),
(2), (4) Date: Jun. 17, 2013

(87) PCT Pub. No.: WO2012/085031
PCT Pub. Date: Jun. 28, 2012

(65) Prior Publication Data
US 2013/0274655 A1 Oct. 17, 2013

Related U.S. Application Data

(60) Provisional application No. 61/432,236, filed on Jan. 13, 2011.

(30) Foreign Application Priority Data

Dec. 21, 2010 (EP) .................................... 10196077

(51) Int. Cl.
*A61M 5/20* (2006.01)
*A61M 5/24* (2006.01)
(Continued)

(52) U.S. Cl.
CPC ................ *A61M 5/20* (2013.01); *A61M 5/24* (2013.01); *A61M 5/326* (2013.01);
(Continued)

(58) Field of Classification Search
CPC .............. A61M 5/2053; A61M 5/3204; A61M 2005/206; A61M 5/46; A61M 2005/208;
(Continued)

(56) References Cited

U.S. PATENT DOCUMENTS 4,833,384 A * 5/1989 Munro ................ A61M 5/1452
128/DIG. 1
6,171,276 B1 * 1/2001 Lippe ..................... A61M 5/20
128/DIG. 1

(Continued)

FOREIGN PATENT DOCUMENTS

EP 2253348 11/2010
JP H021822268 A 7/1990
(Continued)

OTHER PUBLICATIONS

International Search Report for Int. App. No. PCT/EP2011/073513, completed Apr. 13, 2012.
(Continued)

*Primary Examiner* — Imani Hayman
*Assistant Examiner* — Hamza Darb
(74) *Attorney, Agent, or Firm* — Fish & Richardson P.C.

(57) ABSTRACT

The invention relates to an auto-injector (A) for administering a dose of a liquid medicament, comprising of a substantially tubular front-end device adapted to contain a syringe with an injection needle and a barrel containing the dose of the medicament and comprising a needle shroud adapted to rest on the skin of a patient receiving an injection and a reusable back-end device comprising of a housing, a plunger connected to or adapted to engage a stopper providing a fluid tight seal for a distal end of the barrel, a motor for displacing the plunger connected to the stopper, wherein the front-end device is attachable to the back-end device, wherein the needle shroud is slidably arranged with respect to the injection needle and wherein an interlock switch is capable of detecting an axial position (PA, PR) of the needle shroud.

13 Claims, 17 Drawing Sheets

(51) Int. Cl.
  *A61M 5/32* (2006.01)
  *A61M 5/315* (2006.01)

(52) U.S. Cl.
  CPC ......... *A61M 5/3213* (2013.01); *A61M 5/3204* (2013.01); *A61M 2005/206* (2013.01); *A61M 2005/208* (2013.01); *A61M 2005/2073* (2013.01); *A61M 2005/2488* (2013.01); *A61M 2005/31588* (2013.01); *A61M 2205/14* (2013.01); *A61M 2205/52* (2013.01); *A61M 2205/6018* (2013.01); *A61M 2205/6054* (2013.01); *A61M 2205/6072* (2013.01)

(58) Field of Classification Search
  CPC .. A61M 5/20; A61M 5/24; A61M 2005/2488; A61M 5/1452; A61M 5/3213; A61M 2005/31588; A61M 2205/6054; A61M 2205/6072; A61M 2205/52; A61M 2205/6018; A61M 2005/2073
  See application file for complete search history.

(56) References Cited

U.S. PATENT DOCUMENTS

| | | | |
|---|---|---|---|
| 6,183,442 B1* | 2/2001 | Athanasiou | A61B 10/0233 604/154 |
| 2002/0095120 A1 | 7/2002 | Larsen et al. | |
| 2005/0209569 A1* | 9/2005 | Ishikawa | A61M 5/20 604/207 |
| 2011/0004165 A1* | 1/2011 | Iio | A61M 5/20 604/197 |
| 2011/0089789 A1* | 4/2011 | Tang | H02K 5/148 310/68 B |

FOREIGN PATENT DOCUMENTS

| | | |
|---|---|---|
| JP | 2001513371 T | 9/2001 |
| JP | 200353169 T | 10/2003 |
| JP | 2007111518 A | 5/2007 |
| JP | 2009533124 | 9/2009 |
| WO | WO 99/07425 | 2/1999 |
| WO | 99/44657 | 9/1999 |
| WO | WO 01/83005 | 11/2001 |
| WO | WO 2004/004809 | 1/2004 |
| WO | WO 2007/132353 | 11/2007 |
| WO | WO 2009/125582 | 10/2009 |
| WO | WO 2010/073452 | 7/2010 |

OTHER PUBLICATIONS

International Preliminary Report on Patentability in International Application No. PCT/EP2011/073513, dated Jun. 25, 2013, 7 pages.
Rote Liste, "50. Hypophysen-, Hypothalamushormone, andere regulatorische Peptide u. ihre Hemmstoffe," Chapter 50, ed. 2008, 20 pages.

* cited by examiner

AUTO-INJECTOR

CROSS REFERENCE TO RELATED APPLICATIONS

The present application is a U.S. National Phase Application pursuant to 35 U.S.C. §371 of International Application No. PCT/EP2011/073513 filed Dec. 21, 2011, which claims priority to European Patent Application No. 10196077.1 filed Dec. 21, 2010 and U.S. Provisional Patent Application No. 61/432,236 filed Jan. 13, 2011. The entire disclosure contents of these applications are herewith incorporated by reference into the present application.

TECHNICAL FIELD

The invention relates to an auto-injector for administering a dose of a liquid medicament according to the preamble of claim 1.

BACKGROUND

Administering an injection is a process which presents a number of risks and challenges for users and healthcare professionals, both mental and physical.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages to the user from this approach. If the user stops pressing the button/plunger then the injection will also stop. This means that the user can deliver an underdose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, hormone therapies, anticoagulants etc.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring.

U.S. 2002/0095120 A1 discloses an automatic injection device which automatically injects a pre-measured quantity of fluid medicine when a tension spring is released. The tension spring moves an ampoule and the injection needle from a storage position to a deployed position when it is released. The content of the ampoule is thereafter expelled by the tension spring forcing a piston forward inside the ampoule. After the fluid medicine has been injected, torsion stored in the tension spring is released and the injection needle is automatically retracted back to its original storage position.

SUMMARY

It is an object of the present invention to provide an improved re-usable auto-injector.

The object is achieved by an auto-injector according to claim 1.

Preferred embodiments of the invention are given in the dependent claims.

In the context of this specification the term proximal refers to the direction pointing towards the patient during an injection while the term distal refers to the opposite direction pointing away from the patient. The terms "clockwise" and "counter-clockwise" in the context of this specification refer to senses of rotation with the auto-injector pointing with its distal end towards the observer.

According to the invention an auto-injector for administering a dose of a liquid medicament comprises:
- a substantially tubular front-end device adapted to contain a syringe with an injection needle and a barrel containing the dose of the medicament and comprising a needle shroud adapted to rest on the skin of a patient receiving an injection and
- a reusable back-end device comprising
  - a housing,
  - a plunger connected to or adapted to engage a stopper providing a fluid tight seal for a distal end of the barrel,
  - a motor, e.g. an electric motor for displacing the plunger connected to the stopper.

The front-end device is attachable to the back-end device. The needle shroud is slidably arranged with respect to the injection needle. An interlock switch in the back end device is capable of detecting an axial position of the needle shroud in order to determine whether or not the auto-injector is applied against an injection site and to allow or deny the user to start an injection cycle depending on this condition wherein the needle shroud would be translated into a retracted position. This requires a user to follow a sequence of operation, first pressing the auto-injector against the injection site, e.g. a patient's skin and then trigger the injection, e.g. by pushing a button thus improving pre injection needle safety.

The front-end device may be arranged as a re-usable or disposable device. Although the re-usable front-end device requires fewer resources and produces less waste, the disposable front-end device avoids the risk of cross contamination since none of its components will get in contact with more than one patient.

The needle shroud may incorporate an extension arm adapted to interact with the interlock switch so as to communicate the axial position of the needle shroud to the back-end device of the auto-injector.

The back-end device may incorporate a sensor unit for detecting actual parameters of the injection, a memory unit for storing user related data and/or specification parameters and a means to provide a visual, acoustical and/or haptic feedback to the user of the auto-injector. A set of device specification parameters may be stored in the memory unit. The specification parameters may be compared with the actual parameters determined during use of the auto-injector. For example, the force needed to insert the injection needle into the skin may be characterized by the current measured during the needle insertion process. If the measured current is out of specification, the back-end device detects an incorrect use of the auto-injector and may abort the injection. Another possible application includes comparing the initial position of the stopper with a corresponding specification parameter at the beginning of the injection. If the position of stopper is out of specification, the back-end device detects that a used and empty syringe is loaded to the front-end device and may disable the injection mechanism to prevent injuries. The auto-injector may fail to operate when no syringe is inserted into the syringe retainer.

The reusable back-end device may incorporate a plurality of control elements used to activate and control a variety of features of the auto-injector, like activating and de-activating the electric motor that axially translates the plunger to insert and/or retract the injection needle and to inject the dose of the medicament. Furthermore, the speed of the needle insertion or the penetration depth of the injection needle may be controlled and/or time delays may be introduced by the user.

The back-end device may be provided with a variety of user-selectable speed profiles that control the torque provided by the motor to facilitate the needle insertion process and/or to modify the injection speed. Various parameters may be modified to suit the user and/or to drug requirements, like the viscosity of the medication.

The memory unit may be used to store user related data for compliance monitoring. If the patient is on a medication, the back-end device can be used to monitor that the dose of the medicament is administered at correct regular intervals.

The back-end device may have a display, preferably a liquid crystal display, that may visually display injection progress, injection completion, historical user data and/or drug properties, like an expiry date. The display may display messages to remind the patient to take his medicament, specification parameters, an operation mode and/or the type of the medicament contained in the pre-filled syringe. Additionally or alternatively, the back-end device may comprise adequate means to provide an acoustic and/or haptic feedback to the patient and/or the user of the auto-injector.

The sensor unit may detect actual parameters, like the type of medicament or drug contained in the pre-filled syringe in particular by means of radio frequency identification or barcode reading. This allows for an automatic configuration of the auto-injector to properties of the medicament. For example, the penetration depth of the injection needle may be automatically adapted to a depth as required by the medicament.

Additional sensor units may be arranged in particular as micro switches that detect the correct assembly of the auto-injector and/or the correct mounting of the front-end device to the back-end device. The sensor units may also be arranged as encoders, light gates and/or current monitoring systems.

The motor of the auto-injector is powered by an energy supply that may be provided by a set of rechargeable or disposable batteries. The torque provided by the motor may be transferred to the plunger by a gearbox comprising, typically, a plurality of gearwheels and a worm gear. A plurality of gear teeth may be formed to the plunger that are engaged by one of the gearwheels to convert the rotational motion to a linear motion of the plunger as in a rack and pinion gear pair. The gearbox may increase an output torque transferred to the plunger to deliver the required plunger motion and force.

Alternative back-end devices 3 may be arranged without a gearbox. Other forms of gearboxes may likewise be applied—eg a lead screw driven directly or indirectly by the motor.

The direction of the motor may be immediately inverted when the auto-injector is removed from the injection site at any time of the injection allowing for a partial delivery of the dose of the medicament. Upon removal of the auto-injector from the injection site, the injection needle is retracted to reduce the risk of an accidental needle stick. Removal from the injection site may be detected by the needle shroud returning into the advanced position.

An electronic control unit may be arranged within the housing that controls the various features of back-end device and in particular the motor. The electronic control unit may comprise a printed circuit board. A closed loop motion control may be embedded in the electronic control unit that controls the speed of the motor to reduce shock loads on the reusable auto-injector and/or on the syringe and hence reduce the risk of breaking the syringe.

The electronic control unit may be capable of detecting a stall of the motor at the end of the injection stroke delivering the dose of medication to the patient, e.g. by measuring the current through the motor. This indicates that the syringe is completely empty and may trigger the needle retraction mechanism of the auto-injector.

An encoder sensor capable of determining the position of the plunger may be connected to the gearbox. Detection of the position of the plunger may be used to achieve a phased motion of the plunger during the injection. Hence, the translation speed of the plunger may be adapted to the different phases of the drug delivery comprising the needle insertion phase, the expelling of the medicament and the needle retraction phase. Needle insertion is thought to be less painfull to the patient when performed quickly whereas injection is considered less painfull when performed rather slowly.

The encoder sensor may be arranged as a slotted encoder wheel driven by the motor and arranged between an emitter and a sensor of an optical coupler. The encoder sensor may also be a linear sensor.

The auto-injector may preferably be used for subcutaneous or intra-muscular injection, particularly for delivering one of an analgetic, an anticoagulant, insulin, an insulin derivate, heparin, Lovenox, a vaccine, a growth hormone, a peptide hormone, a protein, antibodies and complex carbohydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1A:
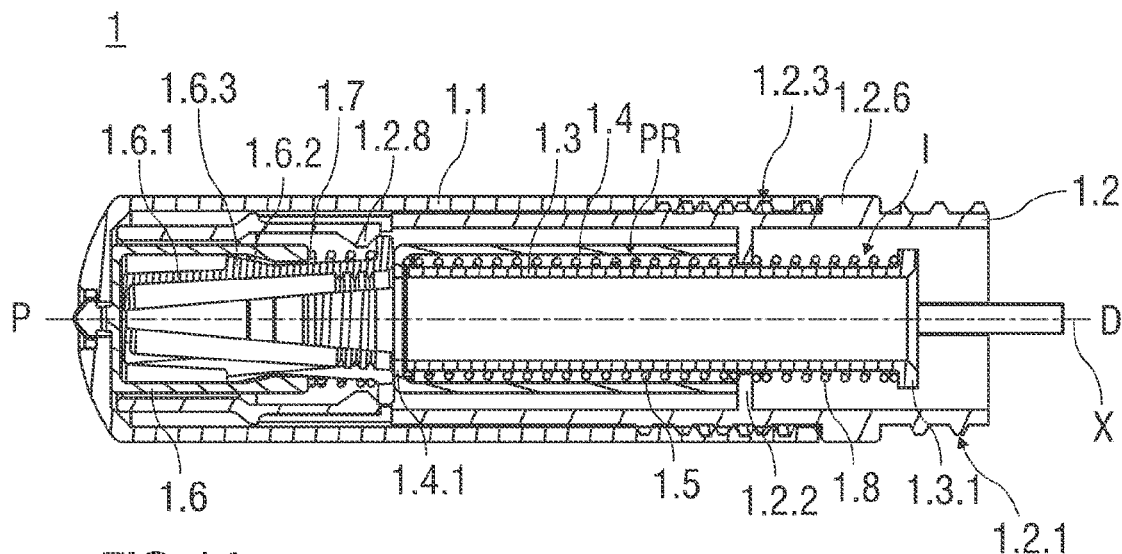
FIGS. 1A and 1B show sectional views of a reusable front-end device of an auto-injector according to a first embodiment of the invention before a pre-filled syringe is loaded into the front-end device.
Figure 1B:
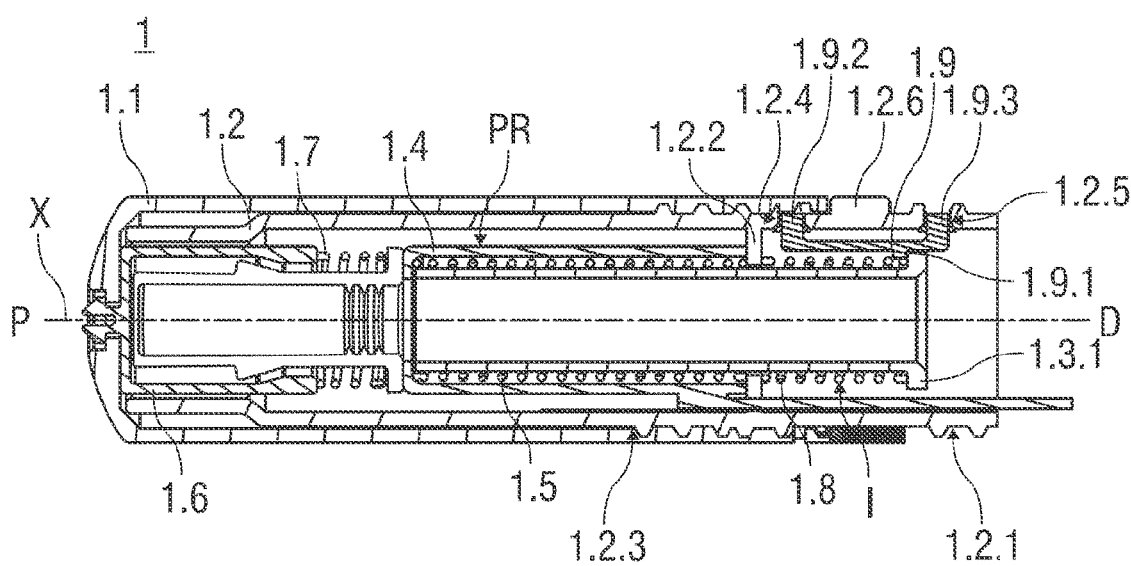

FIGS. 1A and 1B show sectional views of a reusable front-end device 1 of an auto-injector A that is adapted to receive a syringe 2. The front-end device 1 shown in FIGS. 1A and 1B is empty; the syringe 2 that is pre-filled with a dose of a medicament may be inserted into the front-end device 1 before an injection through a distal end of the front-end device 1.

Figure 9A:
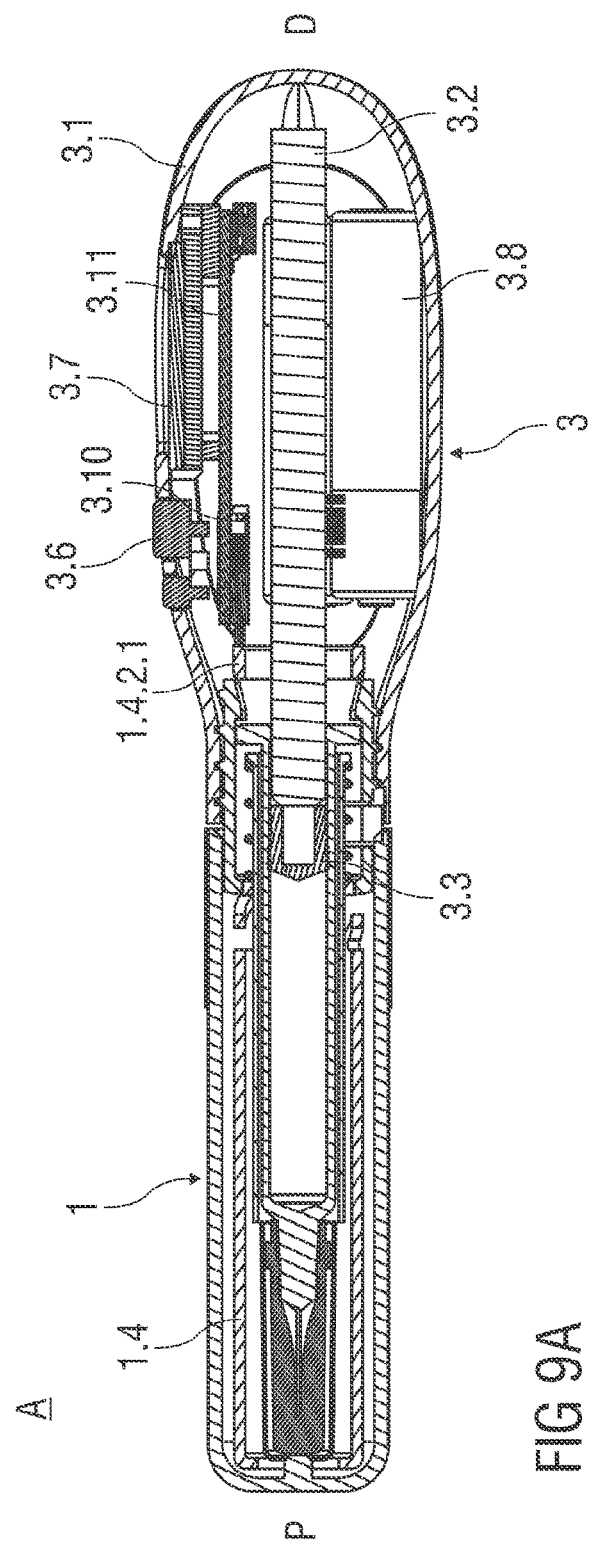
FIGS. 9A and 9B show two sectional views of the auto-injector according to the first embodiment of the invention.
Figure 9B:
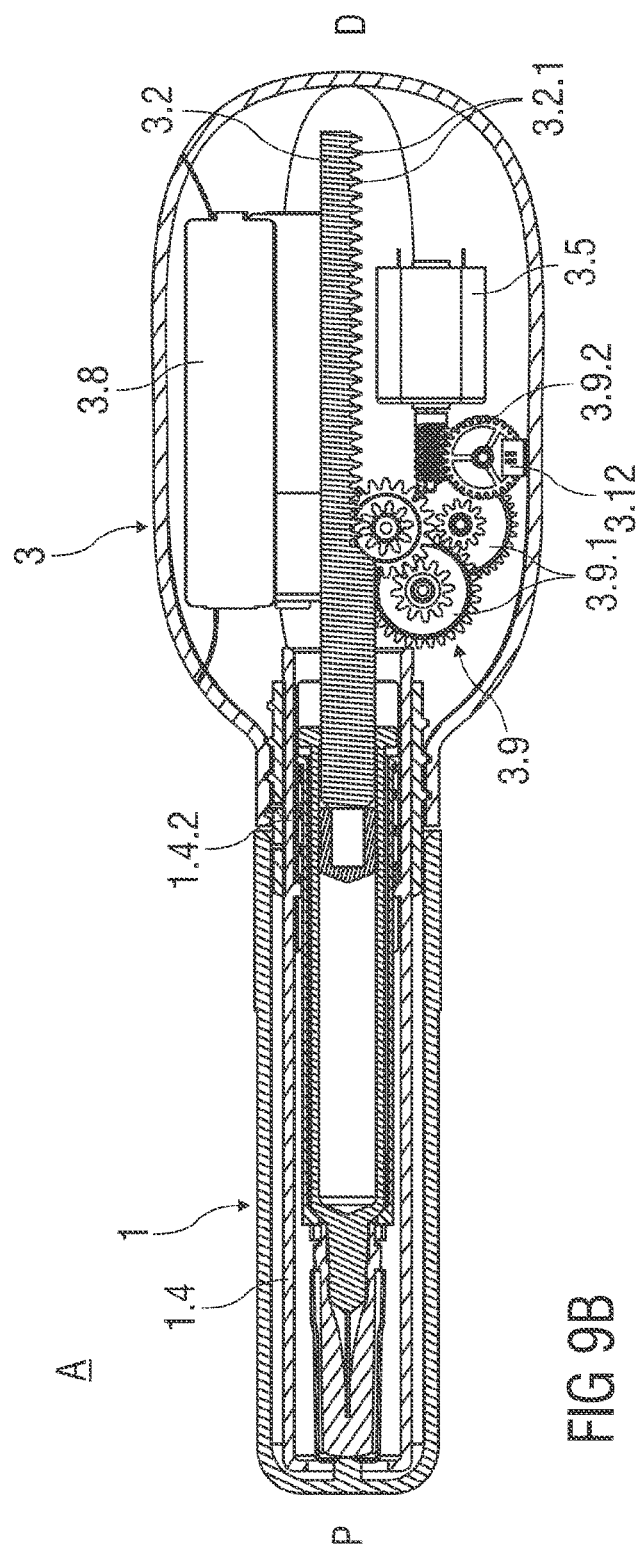

The substantially tubular front-end device 1 is attachable to a proximal end of a reusable back-end device 3 shown in more detail in FIGS. 9A and 9B. The back-end device 3 comprises driving means, like, in particular, an electric motor 3.5 of the auto-injector A.

Figure 2A:
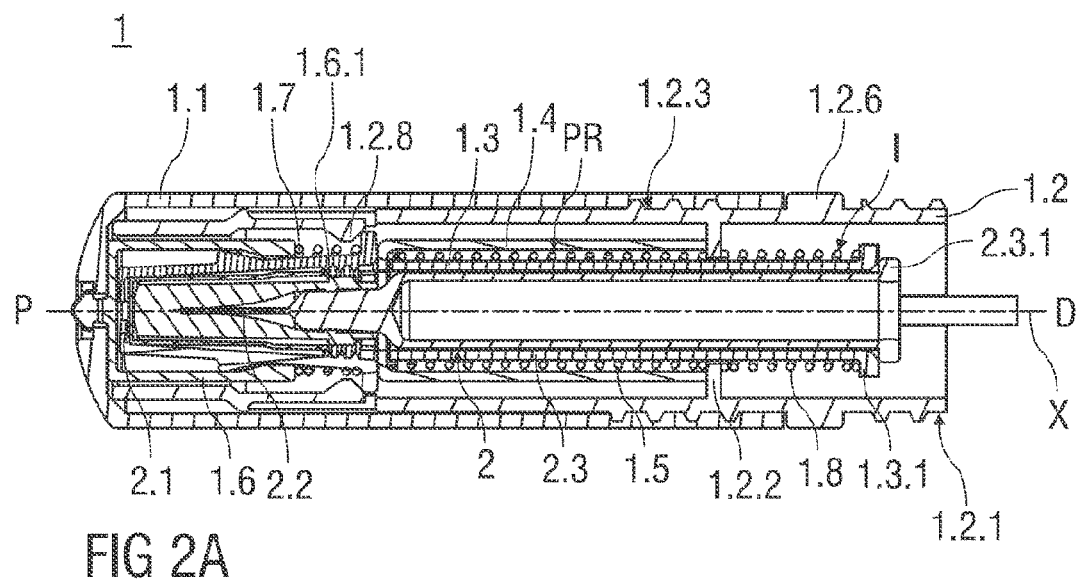
FIGS. 2A and 2B show sectional views of the reusable front-end device of the auto-injector according to the first embodiment of the invention with the syringe inserted into the front-end device.
Figure 2B:
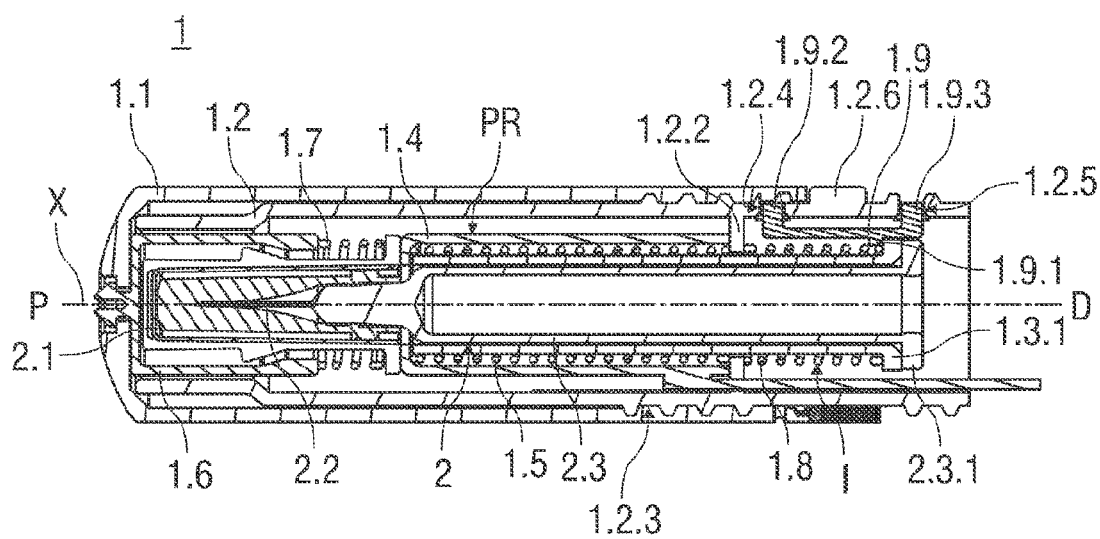

The front-end device 1 comprises a tubular outer sleeve 1.1 with a substantially closed proximal end, a tubular support sleeve 1.2 received within the outer sleeve 1.1 and a tubular syringe retainer 1.3 retained in the support sleeve 1.2. The syringe retainer 1.3 is adapted to receive and mount the pre-filled syringe 2 as shown in FIGS. 2A and 2B A first screw thread 1.2.1 disposed at the distal end of the support sleeve 1.2 provides a means for attaching the front-end device 1 to the back-end device 3. The first screw thread 1.2.1 may be arranged as a right hand screw thread, so that the back-end device 3 may be attached to the front-end device 1 by a clockwise rotation, as viewed from the distal end of the back-end device 3.

A substantially cylindrical needle shroud 1.4 is slidably arranged with respect to the syringe retainer 1.3 and surrounds a proximal section of the syringe retainer 1.3 in a retracted position PR. A pre-tensioned transfer spring 1.5 bears against an annular rib 1.2.2 formed to an inner surface of the support sleeve 1.2 in the distal direction D and against a shoulder 1.4.1 formed to a proximal end of the needle shroud 1.4 to bias the needle shroud 1.4 with respect to the support sleeve 1.2 in the proximal direction P.

The needle shroud 1.4 abuts against two clamp arms 1.6.1 arranged opposite to each other in the proximal direction P, so that the needle shroud 1.4 is retained in the retracted position PR against the biasing force provided by the transfer spring 1.5. The clamp arms 1.6.1 are inserted into a locking sleeve 1.6 firmly connected to the closed proximal end of the outer sleeve 1.1. As best seen in FIG. 1A, the two clamp arms 1.6.1 are splayed in the radial outward direction, so that a protective needle cap 2.1 attached to a proximal tip of the pre-filled syringe 2 may be easily inserted in the intermediate area between the two clamp arms 1.6.1.

A first ramp 1.6.2 is formed to an inner surface of the locking sleeve 1.6 that abuts against a correspondingly formed outward rib 1.6.3, on clamp arm 1.6.1 so that the clamp arms 1.6.1 are deflected radially inwards when the locking sleeve 1.6 is translated parallel to an axis X of the substantially cylindrical front-end device 1 in a proximal direction. A clamp spring 1.7 arranged between the locking sleeve 1.6 and the clamp arms 1.6.1 biases the locking sleeve 1.6 and the clamp arms 1.6.1 away from each other along axis X. The interaction of the first ramp 1.6.2 and the outward rib 1.6.3 redirects the biasing force provided by the clamp spring 1.7 in the radial inward direction. Thus, the clamp arms 1.6.1 are biased radially inwards. Inward movement of the clamp arms 1.6.1 is limited by the axial travel allowed for clamp spring 17.

The needle cap 2.1 may be gripped by the clamp arms 1.6.1 and pulled off the proximal tip of the pre-filled syringe 2 by inserting the pre-filled syringe 2 into the syringe retainer 1.3 and removing the outer sleeve 1.1 from the support sleeve 1.2 of the front-end device 1.

The outer sleeve 1.1 is connected to the support sleeve 1.2 by a second screw thread 1.2.3. The second screw thread 1.2.3 comprises a direction of rotation that is opposite to the one of the first screw thread 1.2.1. As the first screw thread 1.2.1 is designed as a right hand screw thread, the second screw thread 1.2.3 is arranged as a left hand screw thread.

Alternatively, the first screw thread 1.2.1 may be arranged as a left hand screw thread and the second screw thread 1.2.3 may be designed as a right hand screw thread. In this alternative embodiment, the back-end device 3 can be attached to the front-end device 1 by a counter-clockwise rotation.

A radially protruding support collar 1.2.6 is formed to the outer surface of the support sleeve 1.2 between the first screw thread 1.2.1 and the second screw thread 1.2.3. The support collar 1.2.6 acts as a bearing surface for both the first and the second screw thread 1.2.1, 1.2.3. Therefore, a proximal end of the back-end device 3 bears against the support collar 1.2.6 in the proximal direction P when the back-end device 3 is attached to the front-end device 1. Respectively, the outer sleeve 1.1 bears against the support collar 1.2.6 in the distal direction D when the outer sleeve 1.1 is screwed all the way in.

A return spring 1.8 bears against the annular rib 1.2.2 of the support sleeve 1.2 and against a first flange formed to the distal end of the syringe retainer 1.3. When the syringe retainer 1.3 is in a first position I shown in FIGS. 1A and 1B, the return spring 1.8 is in a relaxed or slightly compressed state. An axial translation of the syringe retainer 1.3 with respect to the support sleeve 1.2 in the proximal direction P compresses the return spring 1.8, so that the syringe retainer 1.3 is biased to return to the first position I. The axial translation of the syringe retainer 1.3 with respect to the support sleeve 1.2 in the proximal direction P requires prior removal of the outer sleeve 1.1.

FIG. 1B shows an assembly lock 1.9 arranged at the distal end of the support sleeve 1.2 that comprises a second inward projection 1.9.1. The assembly lock 1.9 comprises an essentially u-shaped cross-section and first and second locking pins 1.9.2, 1.9.3 that protrude into respective first and second orifices 1.2.4, 1.2.5 formed into the support sleeve 1.2. The assembly lock 1.9 is biased in the radial outward direction by a biasing means (not illustrated). The outer sleeve 1.1 screwed onto the support sleeve 1.2 abuts against the first locking pin 1.9.2 and pushes the assembly lock 1.9 radially inwards, so that the second inward projection 1.9.1 latches to the first flange 1.3.1 to prevent a proximal displacement of the syringe retainer 1.3 with respect to the support sleeve 1.2. The syringe retainer 1.3 may be arranged to be prevented from moving in the distal direction D from the first position I. For this purpose the second inward projection 1.9.1 may engage in a recess (not illustrated) in the first flange 1.3.1 or the second inward projection 1.9.1 may be arranged to wrap over the first flange 1.3.1 so as to retain the syringe retainer 1.3 in both directions until the front-end device 1 and the back-end device 3 are assembled together. A spring, e.g. in the shape of a clip may be provided for biasing the assembly lock 1.9 radially outwards.

FIGS. 2A and 2B show sectional views of the front-end device 1 with the pre-filled syringe 2 inserted into the syringe retainer 1.3. The needle cap 2.1 covers an injection needle 2.2 attached to a proximal end of the pre-filled syringe 2. The pre-filled syringe 2 comprises a barrel 2.3 containing the dose of the medicament or drug. A barrel collar 2.3.1 is formed to the distal end of the barrel 2.3 and abuts proximally against the first flange 1.3.1 of the syringe retainer 1.3.

The front-end device 1 may be loaded by inserting the pre-filled syringe 2 into the syringe retainer 1.3. This may be most easily, but not necessarily, achieved by orienting the front-end device 1 vertically. The needle cap 2.1 does not have to be removed before the pre-filled syringe 2 is inserted into the front-end device 1 to provide increased protection from accidental needle stick injuries. The initial radial spacing of clamp arms 1.6.1 is such that the needle cap 2.1 can pass fully between them. A first inward projection 1.2.8 is formed to an inner surface of the support sleeve 1.2 that abuts against the clamp arm 1.6.1. As the outer sleeve is removed from the support sleeve it draws with it the locking sleeve 1.6 and clamp arms 1.6.1. The first inward projection 1.2.8 directs the clamp arm 1.6.1 radially inwards, so that the needle cap 2.1 is firmly gripped by the clamp arms 1.6.1 and may be removed from the proximal tip of the pre-filled syringe 2 by removing the outer sleeve 1.1 from the support sleeve 1.2.

Figure 3:
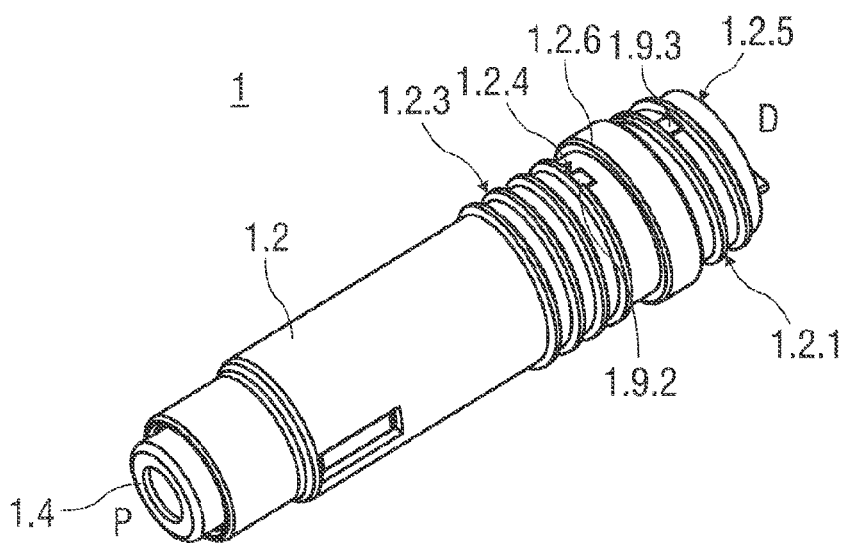
FIG. 3 shows a perspective view of the front-end device according to the first embodiment with the outer sleeve removed from a support sleeve.

FIG. 3 shows a perspective view of the front-end device 1 according to the first embodiment with the outer sleeve 1.1 removed from the support sleeve 1.2. The needle shroud 1.4 is in an advanced position PA and protrudes from the support sleeve 1.2 in the proximal direction P. The first locking pin 1.9.2 of the assembly lock 1.9 protrudes through the first orifice 1.2.4 of the support sleeve 1.2 and may be pushed inwards when the outer sleeve 1.1 is screwed onto the support sleeve 1.2. Respectively, the second locking pin 1.9.3 protrudes through the second orifice 1.2.5 and may engage the back-end device 3.

Figure 4A:
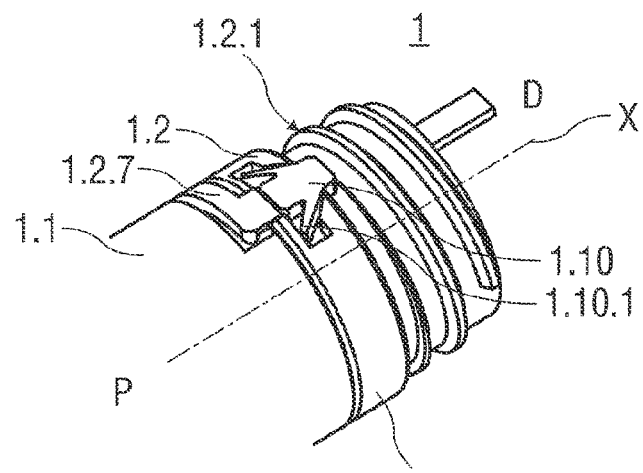
FIGS. 4A and 4B show details of the support sleeve of the front-end device according to the first embodiment in two perspective views.
Figure 4B:
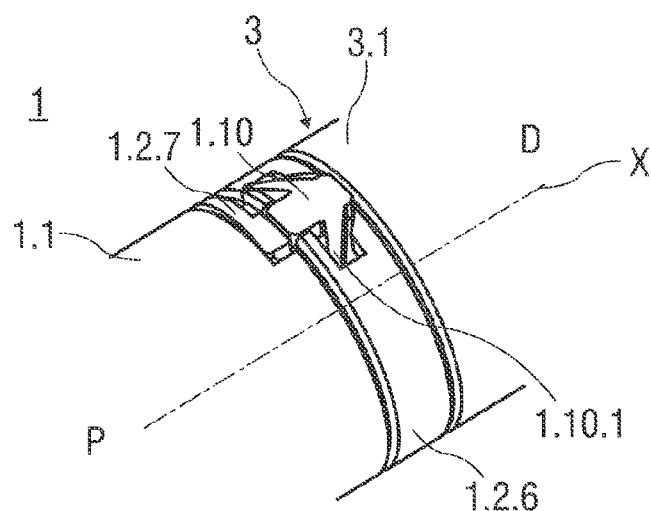

FIGS. 4A and 4B show details of the support sleeve 1.2 of the front-end device 1 in two perspective views. The outer sleeve 1.1 is screwed onto the support sleeve 1.2 and covers a proximal section thereof. A drive dog 1.10 is slidably arranged with respect to the support sleeve 1.2. Two spring arms 1.10.1 are formed to the drive dog 1.10 that bias the drive dog 1.10.1 in the distal direction D. The drive dog 1.10 is slidably mounted to the support collar 1.2.6 separating the first screw thread 1.2.1 and the second screw thread 1.2.3 that is engaged by the outer sleeve 1.1.

FIG. 4A shows the front-end device detached from the back-end device 3. The drive dog 1.10 protrudes from the support collar 1.2.6 in the distal direction D, so that the drive dog 1.10 may be axially translated in the proximal direction P when the back-end device 3 is attached to the front-end device 1 via the first thread connection 1.2.1. The drive dog 1.10 bears against a latch 1.2.7 formed to the distal end of the outer sleeve 1.1. When the front-end device 1 is detached from the back-end device, the latch 1.2.7 latches to the support collar 1.2.6 of the support sleeve 1.2 and rotationally affixes the outer sleeve 1.1 with respect to the support sleeve 1.2.

FIG. 4B shows the front-end device 1 according to the first embodiment attached to the back-end device 3 having a housing 3.1. The front-end device 1 is screwed all the way in, so that the proximal end of the housing 3 of the back-end device 3 pushes the drive dog 1.10 abutting against the latch 1.2.7 in the proximal direction P. The latch 1.2.7 disengages the support collar 1.2.6 and releases the rotational attachment of the support sleeve 1.2 with respect to the outer sleeve 1.1.

Figure 5A:
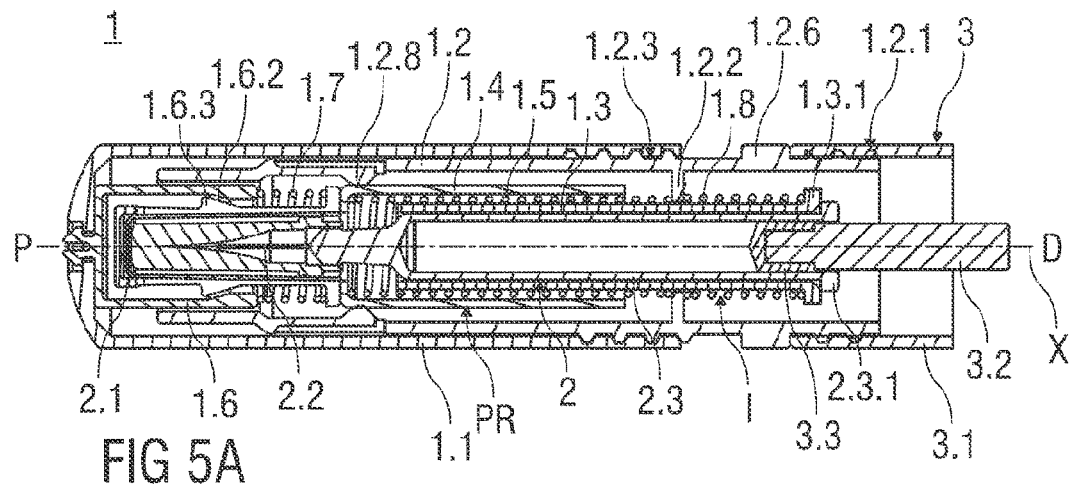
FIGS. 5A and 5B show sectional views of the front-end device according to the first embodiment that is connected to a reusable back-end device of the auto-injector.
Figure 5B:
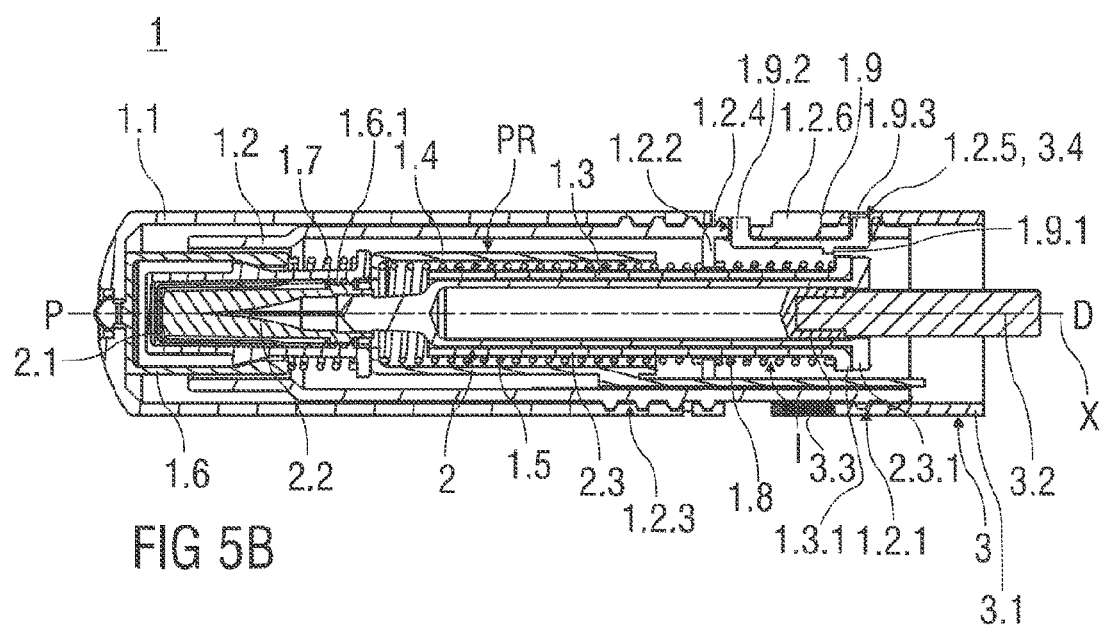

FIGS. 5A and 5B show sectional views of the front-end device 1 according to the first embodiment of the invention that is connected to the back-end device 3 via the first screw thread 1.2.1.

A plunger 3.2 of the back-end device 3 is connected to a stopper 3.3 that is inserted into a distal end of the barrel 2.3 of the pre-filled syringe 2. The stopper 3.3 seals the distal end of the barrel 3.2 in a fluid-tight manner. The plunger 3.2 and the stopper 3.3 may be axially displaced in the proximal direction P to expel the dose of the medicament contained in the pre-filled syringe 2 through the injection needle 2.2 during the injection.

The outer sleeve 1.1 is unscrewed and pulled off the support sleeve 1.2. The axial translation of the outer sleeve 1.1 with respect to the support sleeve 1.2 causes the clamp arms 1.6.1 to constrict in the radial inward direction and clamp to the needle cap 2.1.

Preferably, the needle cap 2.1 is made at least partially from a relative soft plastics material, so that the needle cap 2.1 may be easily gripped by the inwardly deflected clamp arms 1.6.1. The needle cap 2.1 may be arranged as a rubber needle shield or as a rigid needle shield. The rigid needle shield has two apertures in the outer rigid part which would allow the barbs on the clamp arms 1.6.1 to enter, gripping the needle cap 2.1 securely.

As illustrated in FIG. 5B, the proximal displacement of the outer sleeve 1.1 releases the assembly lock 1.9 that prevents a proximal movement of the syringe retainer 1.3 within the support sleeve 1.2. The outer sleeve 1.1 makes way for the first locking pin 1.9.2 of the assembly lock 1.9 to protrude through the first orifice 1.2.4. The assembly lock 1.9 is moved radially outwards, so that the second inward projection 1.9.1 disengages the first flange 1.3.1 to unlock the syringe retainer 1.3. The syringe retainer 1.3 may now move with respect to the support sleeve 1.2 in the proximal direction P.

The second locking pin 1.9.3 of the assembly lock 1.9 protrudes through the second orifice 1.2.5 of the support sleeve 1.2 and into a third orifice 3.4 formed into a proximal end section of the housing 3.1. The assembly lock 1.9 locks the support sleeve 1.2 to the housing 3.1 of the back-end device 3 in a manner to prevent a relative rotation of these parts 1.1, 3. Thus, the support sleeve 1.2 cannot be unscrewed from the back-end device 3 until the outer sleeve 1.1 is re-attached to the support sleeve 1.2.

The auto-injector A comprising the pre-filled syringe 2, the front-end device 1 and the back-end device 3 is assembled before an injection in a particular simple manner. After the pre-filled syringe 2 is inserted in the syringe retainer 1.3 of the front-end device 1 with the outer sleeve 1.1 attached thereto, the outer sleeve 1.1 may be gripped by the user and the back-end device 3 is screwed onto the right-handed first screw thread 1.2.1 by a clockwise rotation. When the first screw thread 1.2.1 bottoms out, the drive dog 1.10 is axially translated in the proximal direction P and releases the latch 1.2.7. A continuous clockwise rotation of the back-end device 3 causes the outer sleeve 1.1 to rotate with respect to the support sleeve 1.2, whereby the left-handed second screw thread 1.2.3 is released.

Alternatively, the back-end device 3 is attachable to the front-end device 1 and the outer sleeve 1.1 is detachable from the support sleeve 1.2 by continuously rotating the back-end device 3 with respect to the outer sleeve 1.1 in a counter-clockwise direction. In this alternative embodiment of the invention, the first screw thread 1.2.1 is arranged as a left-handed screw connection, whereas the second screw thread 1.2.3 is right-handed.

Figure 6:
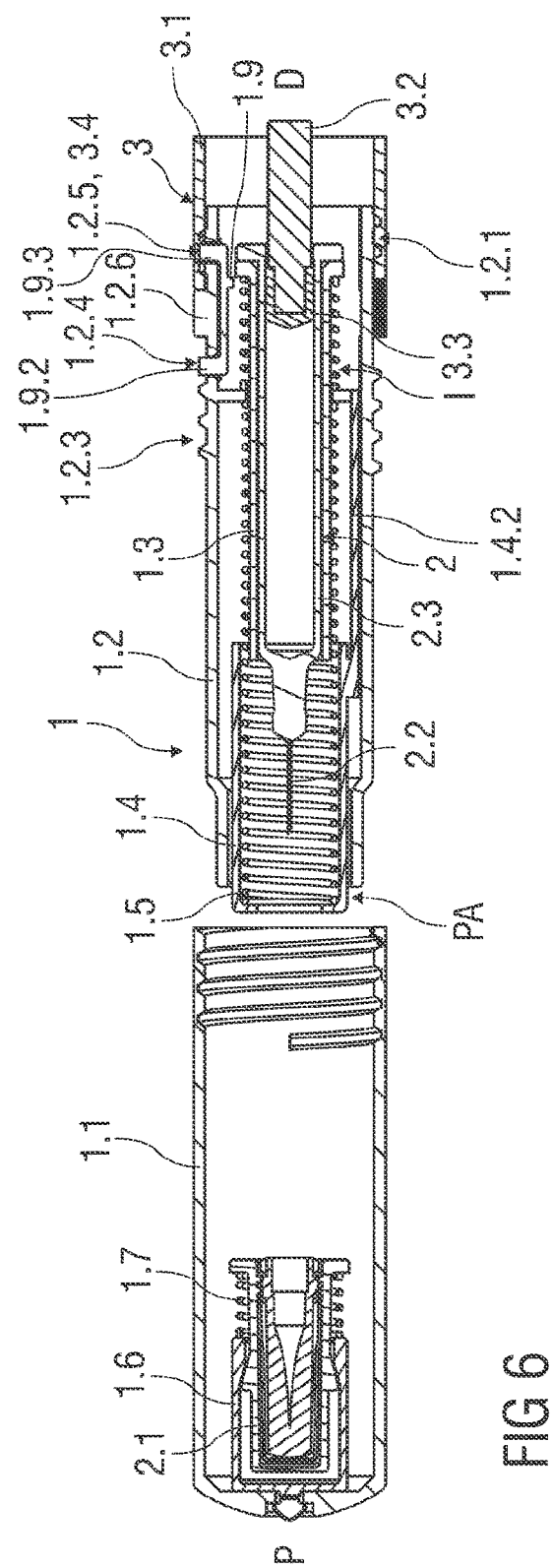
FIG. 6 shows a sectional view of the front-end device according to the first embodiment with the outer sleeve detached therefrom.

FIG. 6 shows a sectional view of the front-end device 1 attached to the back-end device 3 and detached from the outer sleeve 1.1. The needle cap 2.1 is gripped by the clamp arms 1.6.1 that are connected to the outer sleeve 1.1 via the locking sleeve 1.6. The first inward projections 1.2.8 direct the clamp arms 1.6.1 radially inwards to support the clamp arms 1.6.1 clamping to the needle cap 2.1. As the outer sleeve 1.1 is pulled off the support sleeve 1.2, the needle cap 2.1 is removed from the proximal tip of the pre-filled syringe 2.1 and the injection needle 2.2 is exposed. The clamp spring 1.7 maintains a radially inwards directed force upon the clamp arms 1.6.1, so that the needle cap 2.1 is retained within the detached outer sleeve 1.1.

Upon removal of the outer sleeve 1.1, the transfer spring 1.5 relaxes and moves the needle shroud 1.4 to the advanced position PA. In the advanced position PA, the needle shroud 1.4 protrudes the support sleeve 1.2 in the proximal direction P. A proximal end of the needle shroud 1.4 is pushed towards the skin of the patient during the injection.

The needle shroud 1.4 comprises an extension arm 1.4.2 that is adapted to communicate an axial displacement of the needle shroud 1.4 to the back-end device 3. As illustrated in more detail in FIGS. 9A and 9B, a skin interlock shroud 1.4.2.1 may be formed to a distal end to the extension arm 1.4.2 that interacts with an interlock switch 3.10. The interlock switch 3.10 detects the displacement of the needle shroud 3.10 to determine if the needle shroud 1.4 is in contact with the skin of the patient. The back-end device 3 may comprise a mechanism that allows for an activation of the motor 3.5 only if the contact of the needle shroud 1.4 with the skin is detected.

Figure 7:
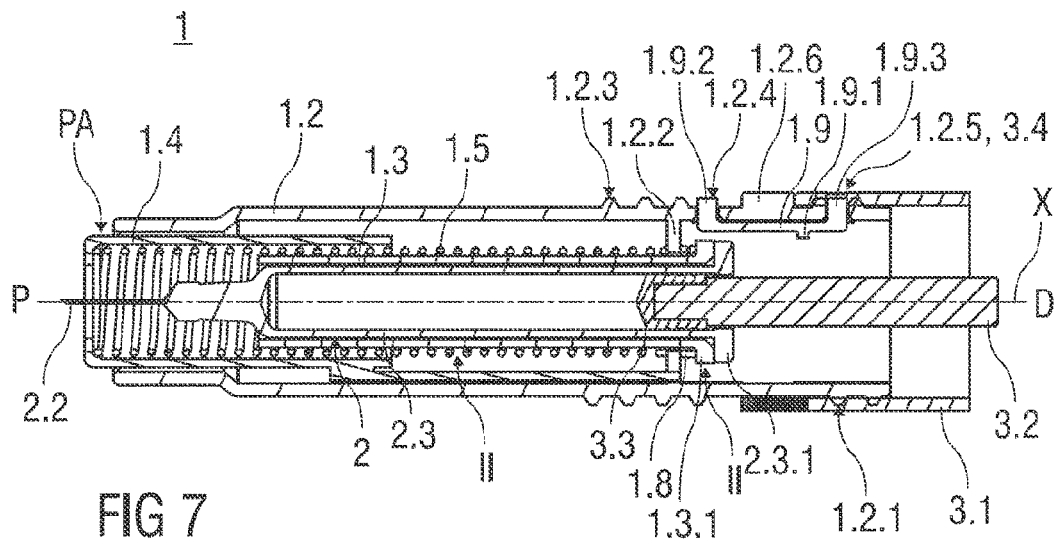
FIG. 7 shows a proximal section of the auto-injector comprising the front-end device according to the first embodiment and the back-end device in mid injection.

FIG. 7 shows a proximal section of the auto-injector A comprising the front-end device 1 and the back-end device 3 in mid injection. The needle shroud 1.4 is pushed against the skin of the patient and the reusable motor 3.5 of the back-end device is activated to drive the syringe retainer 1.3 and the pre-filled syringe 2 retained therein in the proximal direction P to a second position II, whereby the return spring 1.8 is compressed. The injection needle 2.2 protrudes from the needle shroud 1.4 proximally in the second position II and punctures the skin of the patient. A maximal penetration depth of the injection needle 2.2 is limited by the annular rib 1.2.2 that limits the proximal displacement of the syringe retainer 1.3 holding the pre-filled syringe 2 with respect to the support sleeve 1.2.

The stopper 3.3 connected to the plunger 3.2 is driven by the motor 3.5 of the back-end device 3 in the proximal direction P and depressed into the barrel 2.3 of the pre-filled syringe 2, whereby the dose of the medicament is expelled through the injection needle 2.2 and disposed beneath the skin of the patient.

Figure 8:
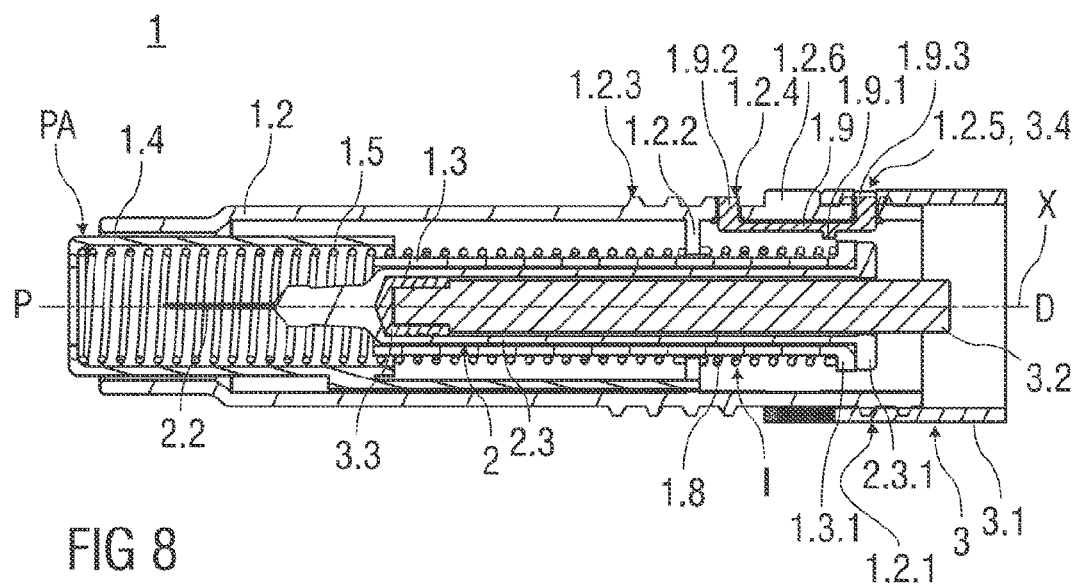
FIG. 8 shows the proximal section of the auto-injector comprising the front-end device according to the first embodiment and the back-end device after injection of the medicament.

FIG. 8 shows the proximal section of the auto-injector A according to the first embodiment comprising the front-end device 1 and the back-end device 3 after injection of the medicament. The plunger 3.2 has been released or actively withdrawn allowing retraction of the syringe 2. The compressed return spring 1.8 relaxes and drives the syringe retainer 1.3 back to the first position I, whereby the injection needle 2.2 of the syringe 2 is withdrawn from the skin of the patient.

Alternatively or additionally, the motor direction of the motor 3.5 is reversed to retract the syringe 2 and the syringe retainer 1.3 to the first position I.

The auto-injector A is then removed from the injection site. The assembly lock 1.9 is locked and prevents a relative rotation between the support sleeve 1.2 of the front-end device 1 and the housing 3.1 of the back-end device 3. Thus, the auto-injector A may not be disassembled until the outer sleeve 1.1 is screwed back onto the support sleeve 1.2 to unlock the assembly lock 1.1. This mechanism forces the user performing the injection to re-attach the needle cap 2.1 retained within the outer sleeve 1.1 onto the proximal tip of the syringe 2 after the injection, so that the injection needle 2.2 is covered when the syringe 2 is removed from syringe retainer 1.3 of the front-end device 1.

The outer sleeve 1.1 is re-attached to the support sleeve 1.2 as illustrated in FIGS. 5A and 5B. As the outer sleeve 1.1 is screwed onto the support sleeve 1.2, the inner surface of the outer sleeve 1.1 engages the first locking pin 1.9.2 protruding radially outwards through the first orifice 1.2.4 and pushes the assembly lock 1.9 radially inwards. The second locking pin 1.9.3 disengages the third orifice 3.4 formed into the housing 3 of the back-end device 3, so that the back-end device 3 is allowed to rotate relative to the support sleeve 1.2 and may be disassembled from the front-end device 1.

The clamp arms 1.6.1 connected to the outer sleeve 1.1 via the locking sleeve 1.6 bear against the needle shroud 1.4 in the distal direction D and push the needle shroud 1.4 back to the retracted position PR. The needle cap 2.1 slides back onto the proximal tip of the syringe 2 to re-sheathe the injection needle 2.2 after the injection.

As can be seen in FIGS. 2A and 2B, the front-end device 1 is detached from the back end-device 3 when the outer sleeve 1.1 engaging the second screw thread 1.2.3 is screwed all the way in. The needle shroud 1.4 in the retracted position PR bears against the clamp arms 1.6.1 in the proximal direction P and splays the clamp arms 1.6.1 radially outwards. The clamp arms 1.6.1 disengage the needle cap 2.1 that frictionally engages the proximal tip of the syringe 2 and covers the used injection needle 2.2. The empty syringe 2 may now be safely removed from the syringe retainer 1.3 of the re-useable front-end device 1 and disposed. The clamp arms 1.6.1 may be integrally moulded in a radially outward position so they would not need to be splayed apart but just allowed to relax towards their radial outward position. The clamp arms 1.6.1 may likewise be made from spring steel or an additional spring could be provided for splaying them apart.

FIGS. 9A and 9B show sectional views of the assembled auto-injector A comprising a similar front-end device 1, the syringe 2 and the back-end device 3. The cross-section shown in FIG. 9A extends perpendicularly to the one shown in FIG. 9B. The housing 3.1 of the back-end device 3 comprises substantially oval cross-sections of different dimensions.

The reusable back-end device 3 of the auto-injector A comprises a plurality of control elements 3.6 used to activate and control a variety of features of the auto-injector A, such as activating and de-activating the electric motor 3.5 that axially translates the plunger 3.2 to insert and/or retract the injection needle 2.2 and to inject the dose of the medicament. Furthermore, the speed of the needle insertion or the penetration depth of the injection needle 2.2 may be controlled and/or time delays may be introduced by the user. The back-end device 3 may be provided with a variety of user-selectable speed profiles that control the torque provided by the motor to facilitate the needle insertion process and/or to modify the injection speed. Various parameters may be modified to suit the user and/or to drug requirements, like the viscosity of the medication.

The back-end device 3 may comprise a memory unit (not illustrated) that may be used to store user related data for compliance monitoring. If the patient is on a medication, the back-end device 3 can be used to monitor that the dose of the medicament is administered at correct regular intervals. Furthermore, a set of device specification parameters may be stored in the memory unit. The specification parameters may be compared with actual parameters determined during use of the auto-injector A. For example, the force needed to insert the injection needle 2.2 into the skin is characterized by the current measured during the needle insertion process. If the measured current is out of specification, the back-end device 3 detects an incorrect use of the auto-injector A and may abort the injection. Another possible application includes comparing the initial position of the stopper 3.3 with a corresponding specification parameter at the beginning of the injection. If the position of stopper 2.5 is out of specification, the back-end device 3 detects that a used and empty syringe 2 is loaded to the front-end device 1 and may disable the injection mechanism to prevent injuries. The auto-injector A may fail to operate when no syringe 2 is inserted into the syringe retainer 1.3.

The back-end device 3 has a display 3.7, preferably a liquid crystal display (LCD), that may visually display injection progress, injection completion, historical user data and/or drug properties, like an expiry date. The display 3.7 may display messages to remind the patient to take his medicament, specification parameters, an operation mode and/or the type of the medicament contained in the pre-filled syringe 2. Additionally or alternatively, the back-end device 3 may comprise adequate means to provide an acoustic and/or haptic feedback to the patient and/or the user of the auto-injector A.

The back-end device 3 may comprise a sensor unit (not illustrated) capable of detecting actual parameters, like the type of medicament or drug contained in the pre-filled syringe 2 in particular by means of radio frequency identification (RFID) or barcode reading. This allows for an automatic configuration of the auto-injector A to properties of the medicament. For example, the penetration depth of the injection needle 2.2 may be automatically adapted to a depth as required by the medicament. The auto-injector A is particularly suited to be used for administering a variety of drugs that may require an intradermal, a transcutaneous or an intramuscular injection.

Additional sensor units (not illustrated) may be arranged in particular as micro switches that detect the correct assembly of the auto-injector A and/or the correct mounting of the front-end device 1 to the back-end device 3. The sensor units may also be arranged as encoders, light gates and/or current monitoring systems.

The motor 3.5 of the auto-injector A is powered by an energy supply 3.8 that may be provided by a set of rechargeable or disposable batteries. The torque provided by the motor 3.5 is transferred to the plunger 3.2 by a gearbox 3.9 comprising a plurality of gearwheels 3.9.1 and a worm gear 3.9.2. A plurality of gear teeth 3.2.1 are formed to the plunger 3.2 that are engaged by one of the gearwheels 3.9.1 to convert the rotational motion to a linear motion of the plunger 3.2 as in a rack and pinion gear pair. The gearbox 3.9 in particular increases the output torque transferred to the plunger 3.2 to deliver the required plunger motion and force.

Alternative back-end devices 3 may be arranged without a gearbox. Other forms of gearboxes may likewise be applied—eg a lead screw driven directly or indirectly by the motor. Other motors with built in gear boxes or linear motors may also be used.

A distal displacement of the interlock shroud 1.4.2.1 connected to the needle shroud 1.4 may be detected by the interlock switch 3.10. The detected distal position PA, PR of the needle shroud 1.4 indicates whether or not the auto-injector A is correctly placed onto the skin of the patient so that the dose of medication may be injected. The back-end device 3 may be programmed in a manner that allows for an activation of the motor 3.5 only if the needle shroud 1.4 is in contact with the skin of the patient. Furthermore, the direction of the motor 3.5 may be immediately inverted when the auto-injector A is removed from the injection site at any time of the injection allowing for a partial delivery of the dose of the medicament. Upon removal of the auto-injector A from the injection site, the injection needle 2.2 is retracted to reduce the risk of an accidental needle stick. Removal from the injection site may be detected by the needle shroud 1.4 returning into the advanced position PA.

An electronic control unit 3.11 is arranged within the housing 3.1 that controls the various features of back-end device 3 and in particular the motor 3.5. The electronic control unit 3.11 may comprise a printed circuit board (PCB). A closed loop motion control may be embedded in the electronic control unit 3.11 that controls the speed of the motor 3.5 to reduce shock loads on the reusable auto-injector A and/or on the syringe 2 and hence reduce the risk of breaking the syringe 2.

The electronic control unit 3.11 is capable of detecting a stall of the motor 3.5 at the end of the injection stroke delivering the dose of medication to the patient. This indicates that the syringe 2 is completely empty and may trigger the needle retraction mechanism of the auto-injector A.

An encoder sensor 3.12 capable of determining the position of the plunger 3.2 is connected to the gearbox 3.9. Detection of the position of the plunger 3.2 is used to achieve a phased motion of the plunger 3.2 during the injection. Hence, the translation speed of the plunger 3.2 may be adapted to the different phases of the drug delivery comprising the needle insertion phase, the expelling of the medicament and the needle retraction phase. Needle insertion is thought to be less painfull to the patient when performed quickly whereas injection is considered less painfull when performed rather slowly.

The front-end device 1 shown in FIGS. 9a and 9b is a disposable one. However, the re-usable back-end device 3 may be combined with the front-end device 1 according to the first embodiment illustrated in FIGS. 1 to 8.

Figure 10A:
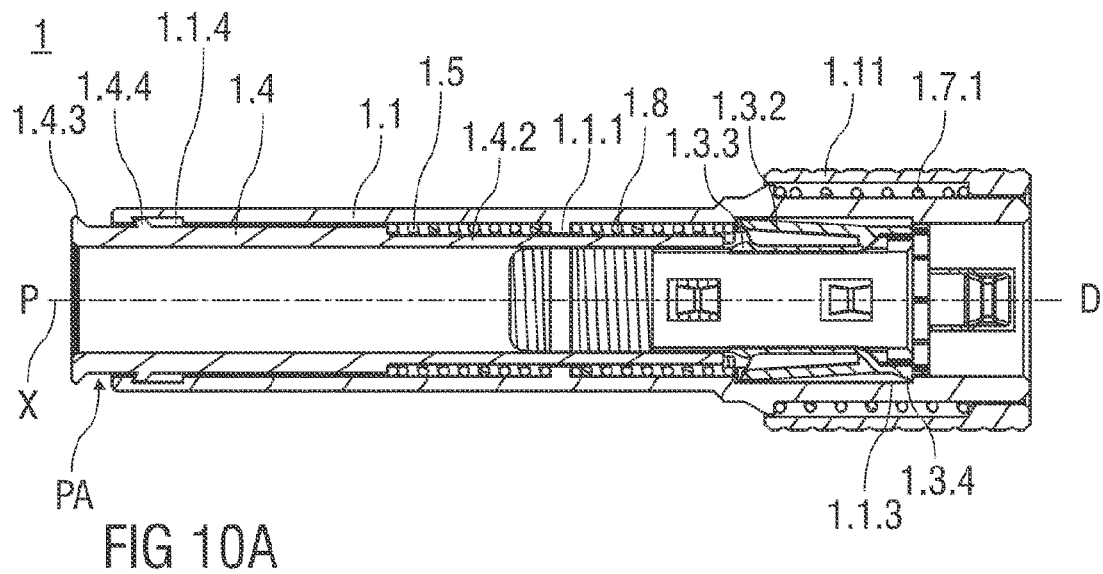
FIGS. 10A and 10B show sectional views of a reusable front-end device according to a second embodiment of the invention before a pre-filled syringe is loaded into the front-end device.
Figure 10B:
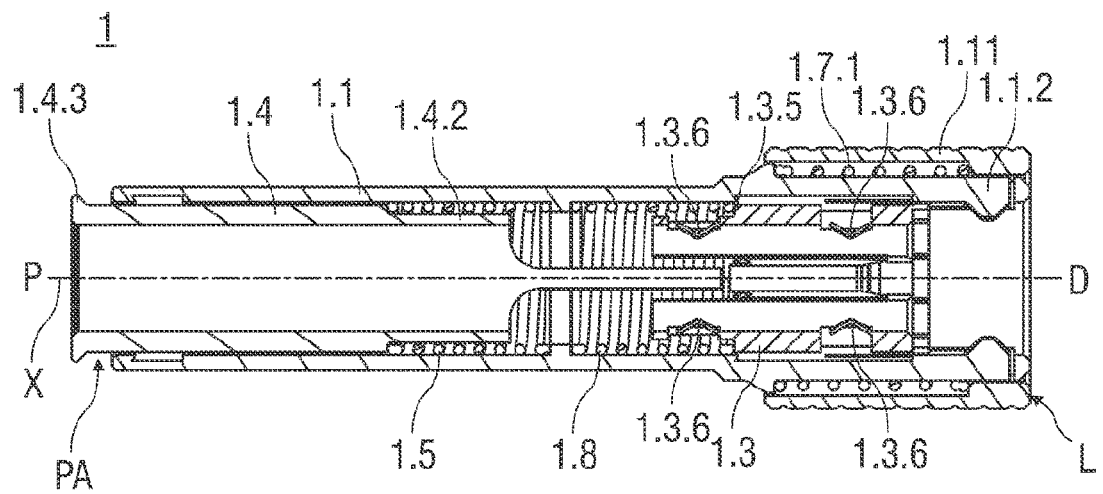

FIGS. 10A and 10B show sectional views of a reusable front-end device 1 according to a second embodiment of the invention.

An auto-injector A comprises the substantially cylindrical front-end device 1, the reusable back-end device 3 and a syringe 2 that is insertable into the front-end device 1. The front-end device 1 is attachable to the reusable back-end device 3 via a compression connection means. The back-end device 3 provides the auto-injector A with a variety of features as described herein before. In particular, the back-end device 3 comprises components as described herein before.

FIGS. 10A and 10B show the front-end device 1 before the syringe 2 containing a dose of a liquid medicament is loaded thereto.

Figure 15A:
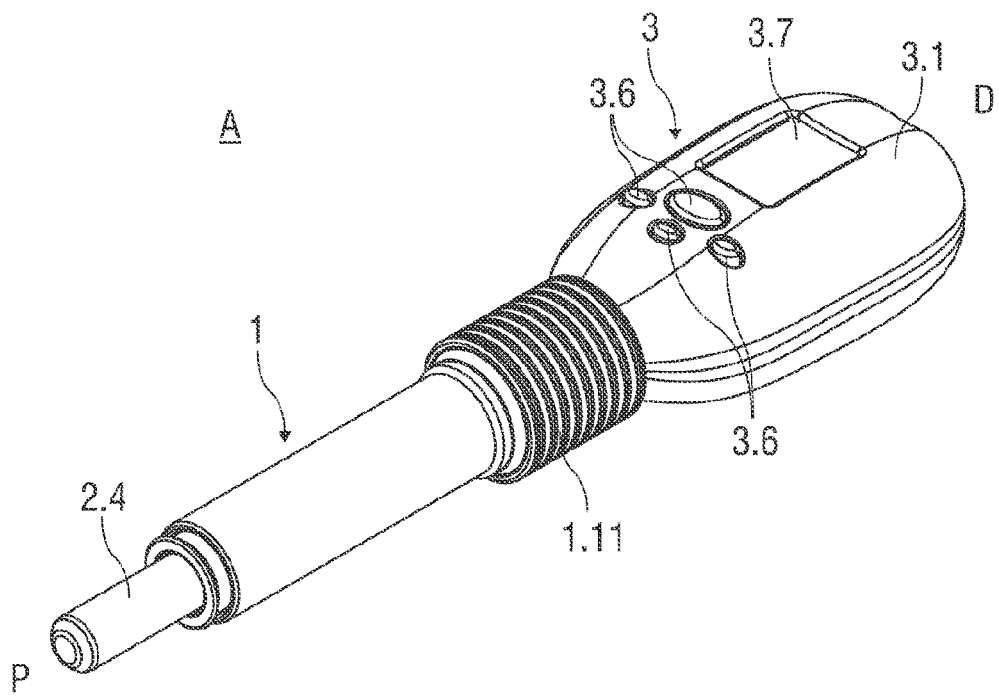
FIGS. 15A and 15B show the assembled auto-injector comprising the back end-device 3 and the front-end device according to the second embodiment in a perspective and a sectional view.
Figure 15B:
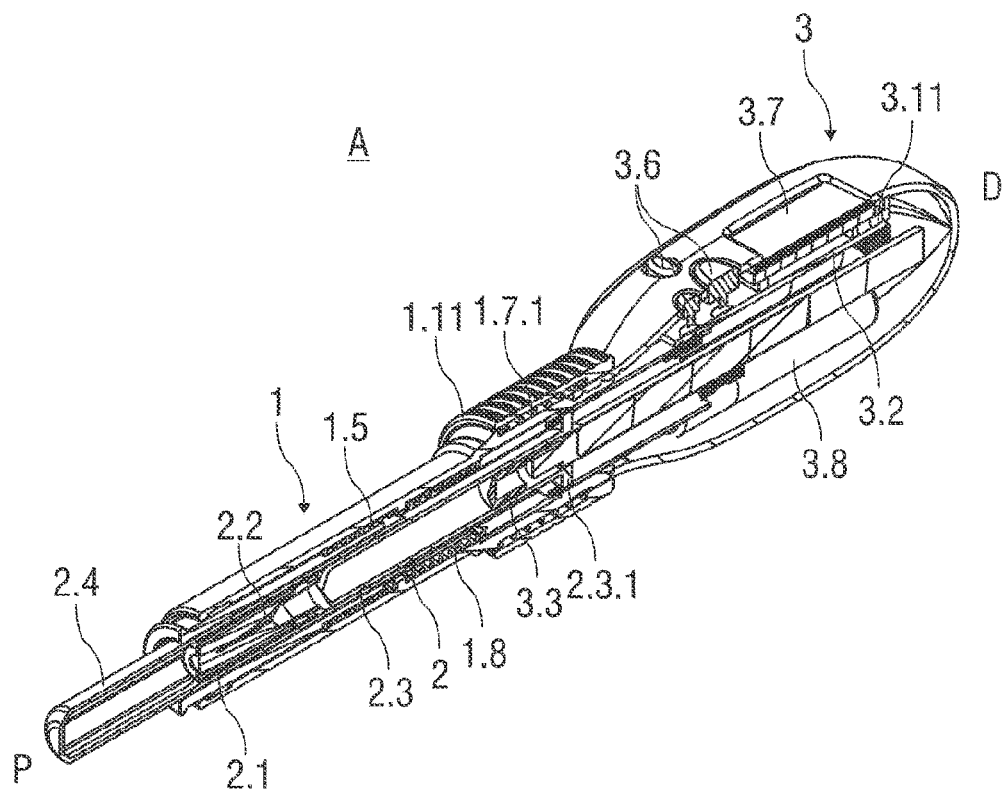

The back-end device 3 shown in FIGS. 15A and 15B) comprises driving means, like an electric motor 3.5 of the auto-injector A that may be activated to translate the pre-filled syringe 2 within the front-end device 1 parallel to an axis X of the substantially cylindrical front-end device 1 and to expel the medicament contained in the pre-filled syringe 2.

The front-end device 1 according to the second embodiment of the invention comprises a tubular outer sleeve 1.1, a syringe retainer 1.3 adapted to receive the syringe 2, an annular mounting sleeve 1.11 and a substantially cylindrical needle shroud 1.4. The needle shroud 1.4 and the syringe retainer 1.3 are slidably arranged with respect to the outer sleeve 1.1.

An annular projection 1.1.1 is formed to an inner surface of the outer sleeve 1.1 and projects in the radial inward direction. A transfer spring 1.5 bears against the needle shroud 1.4 in the proximal direction P and against the annular projection 1.1.1 in the distal direction D to bias the needle shroud 1.4 in the proximal direction P. The needle shroud 1.4 is located in an advanced position PA and protrudes the outer sleeve 1.1 of the front-end device 1 in the proximal direction P.

At least on but preferably two or more flexible arms 1.3.2 are formed to lateral walls of the syringe retainer 1.3. The flexible arms 1.3.2 are arranged on opposite sides of the syringe retainer 1.3 and latch to the outer sleeve 1.1 to prevent an axial translation of the syringe retainer 1.3 when the pre-filled syringe 2 is loaded therein. The flexible arm 1.3.2 comprises an inner release ramp 1.3.3 that may be engaged by an extension arm 1.4.2 formed to the needle shroud 1.4 and projecting therefrom in the distal direction D. The extension arm 1.4.2 engaging the release ramp 1.3.3 unlatches the flexible arm 1.3.2 and releases the syringe retainer 1.3, so that the syringe retainer 1.3 may be axially displaced in the proximal direction with respect to the outer sleeve 1.1.

A longitudinal first recess 1.1.3 is formed into an inner surface of a distal section of the outer sleeve 1.1 parallel to a longitudinal axis X. The first recess 1.1.3 accommodates a first catch 1.3.4 formed to an outer surface of the syringe retainer 1.3. The first catch 1.3.4 is retained in first recess 1.1.3 so as to limit the axial displacement of the syringe retainer 1.3 relative to the outer sleeve 1.1 in the distal direction D.

A return spring 1.8 bears proximally against the annular projection 1.1.1 and against a circumferential bearing surface 1.3.5 of the syringe retainer 1.3 in the distal direction D. The return spring 1.8 biases the syringe retainer 1.3 with respect to the outer sleeve 1.1 in the distal direction D.

A radially protruding annular flange 1.4.3 is formed to a proximal end of the needle shroud 1.4. The annular flange 1.4.3 is adapted to rest on the skin of the patient during the injection. A second catch 1.4.4 projects radially outwards from an outer surface of the needle shroud 1.4 and into a second recess 1.1.4 formed into an inner surface of the outer sleeve 1.1. The second catch 1.4.4 travels along the second recess 1.1.4 and limits a maximal axial displacement of the needle shroud 1.4 relative to the outer sleeve 1.1.

The annular mounting sleeve 1.11 encompasses a distal section of the outer sleeve 1.1 and is slidably arranged with respect thereto. A mounting sleeve spring 1.7.1 that is arranged as a compression spring biases the mounting sleeve 1.11 with respect to the outer sleeve 1.1 in the distal direction D towards a locked position L. In the locked position L, the mounting sleeve 1.11 provides a counter bearing for latch arms 1.1.2 shown in FIG. 10B.

At least on but preferably two or more latch arms 1.1.2 are formed to opposite sides of the distal section of the outer sleeve 1.1 that may latch to a housing 3.1 of the back-end device 3 to mount the front-end device 1 thereto. The mounting sleeve 1.11 abuts against the latch arms 1.1.2 in the radial inward direction to prevent an outward deflection of the latch arms 1.1.2. The mounting sleeve 1.11, the mounting sleeve spring 1.7.1 and the latch arms 1.1.2 provide the compression connection means that mounts the front-end device 1 to the back-end device 3 of the auto-injector A.

As best seen in FIG. 10B, a plurality of radially inwards projecting retaining projections 1.3.6 are formed to an inner surface of the syringe retainer 1.3 that are adapted to frictionally engage a barrel 2.3 of the syringe 2.

Figure 11A:
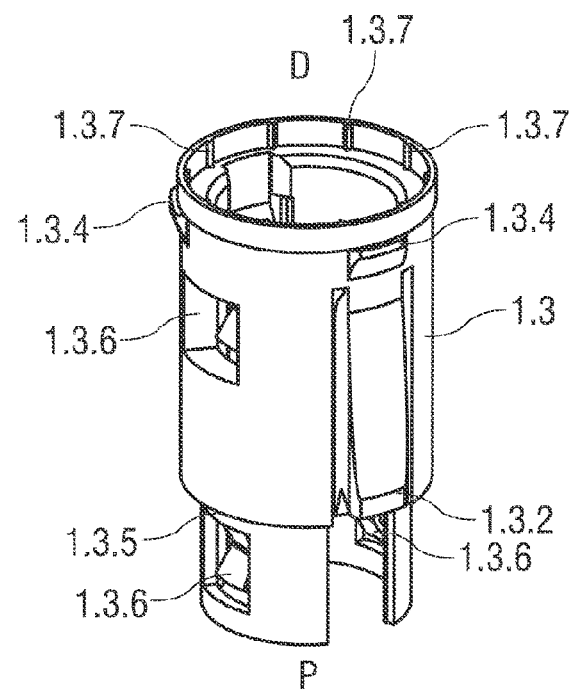
FIGS. 11A and 11B show a syringe retainer according to the second embodiment in different perspective views.
Figure 11B:
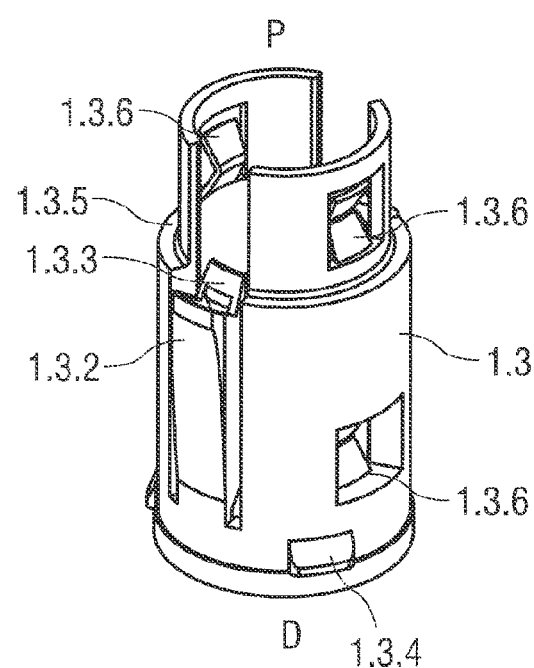

FIGS. 11A and 11B show the syringe retainer 1.3 in different perspective views. The syringe retainer 1.3 features the first catches 1.3.4, the bearing surface 1.3.5, the retaining projections 1.3.6 and the flexible arms 1.3.6 comprising the release ramps 1.3.6. A plurality of friction ribs 1.3.7 is formed to a distal end of the syringe retainer 1.3. The friction rib 1.3.7 protrudes radially inwards and is adapted to frictionally engage a barrel collar 2.3.1 of the syringe 2 and mount the syringe 2 to the syringe retainer 1.3. (As illustrated in FIG. 12B)

Figure 12A:
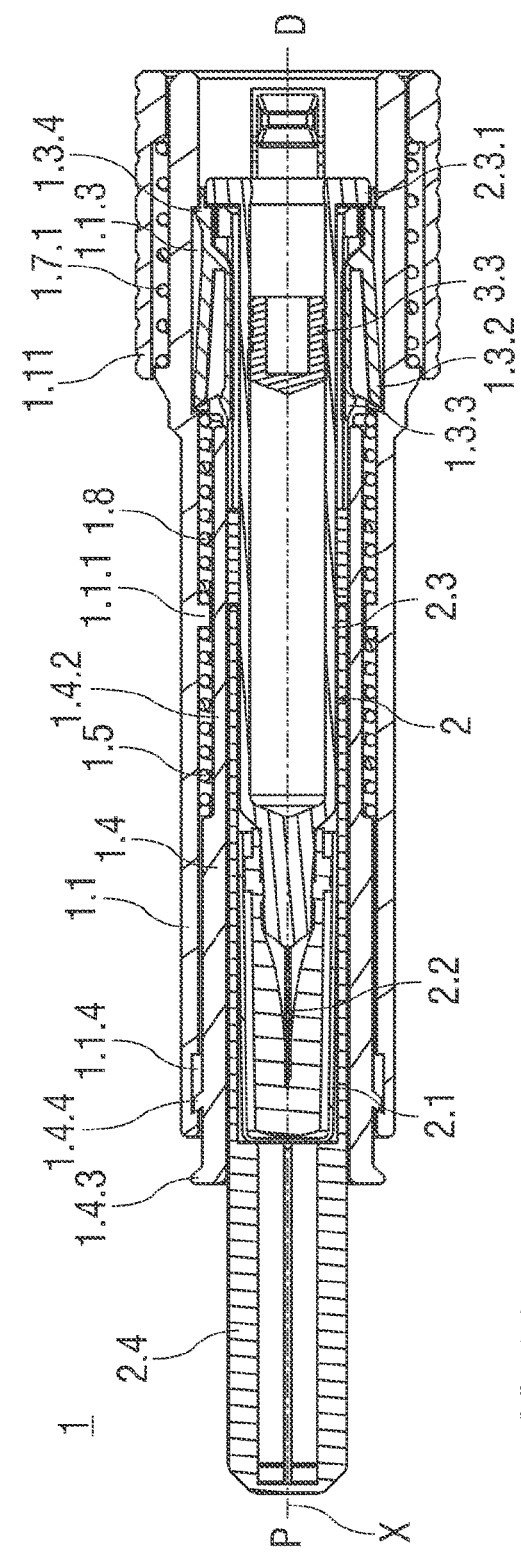
FIGS. 12A and 12B show two different sectional views of the front-end device during syringe assembly
Figure 12B:
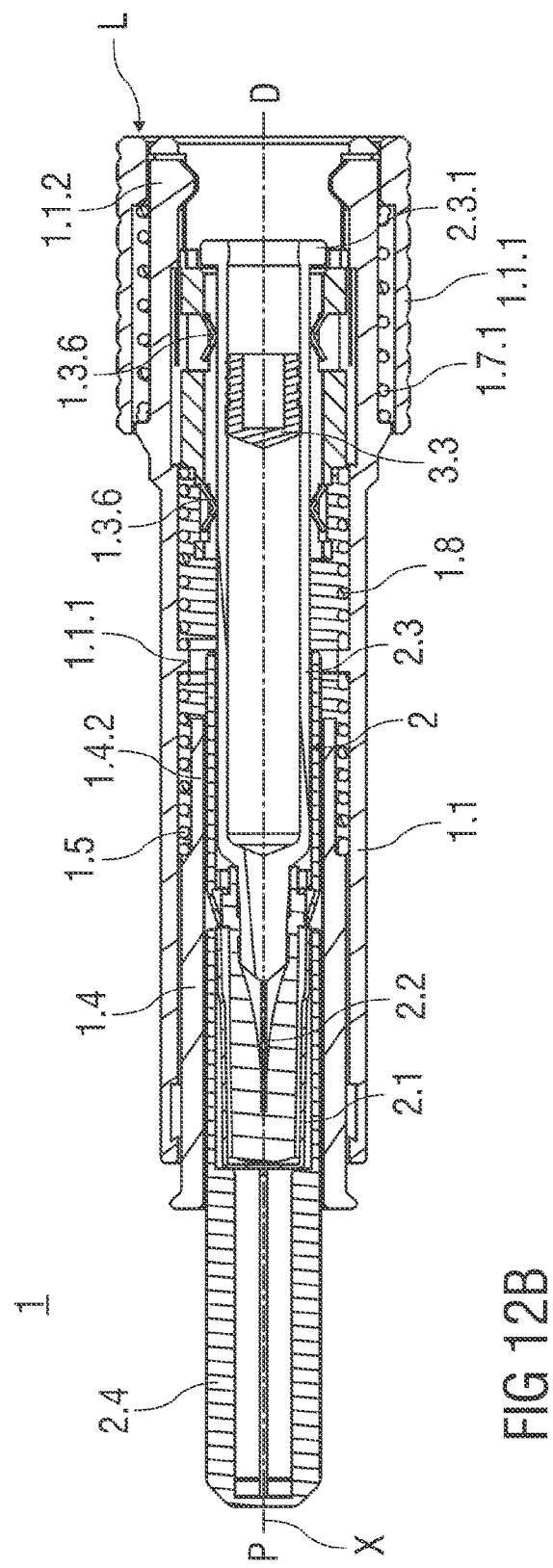

FIGS. 12A and 12B show two different sectional views of the front-end device 1 according to the second embodiment of the invention. The pre-filled syringe 2 is inserted into the syringe retainer 1.3 that is retained in a retracted first position I, so that an injection needle 2.2 attached to the proximal tip of the pre-filled syringe 2 is retained within the front-end device 1.

The syringe 2 comprises a stopper 3.3 that liquid tightly seals the barrel 2.3 and is connectable to a plunger 3.2 of the back-end device 3. The stopper 3.3 may be displaced in the proximal direction P to expel the dose of the medicament contained in the barrel 2.3 through the injection needle 2.2 of the pre-filled syringe 2.

The injection needle 2.2 is covered by a needle cap 2.1. Before or after the syringe 2 is inserted into the front end device 1, an elongated tubular cover 2.4 is attached to the proximal end of the syringe 2, snapping on to the needle cap 2.1 by means of snaps (see FIG. 3) and thus retained. The tubular cover 2.4 projects from the proximal end of the front-end device 1 when the syringe 2 is inserted therein. The tubular cover 2.4 may be easily gripped and pulled in the proximal direction P to remove the needle cap 2.1 from the proximal tip of the pre-filled syringe 2.

Alternatively, the needle cap 2.1 and the tubular cover 24 may be arranged as one piece.

Figure 13A:
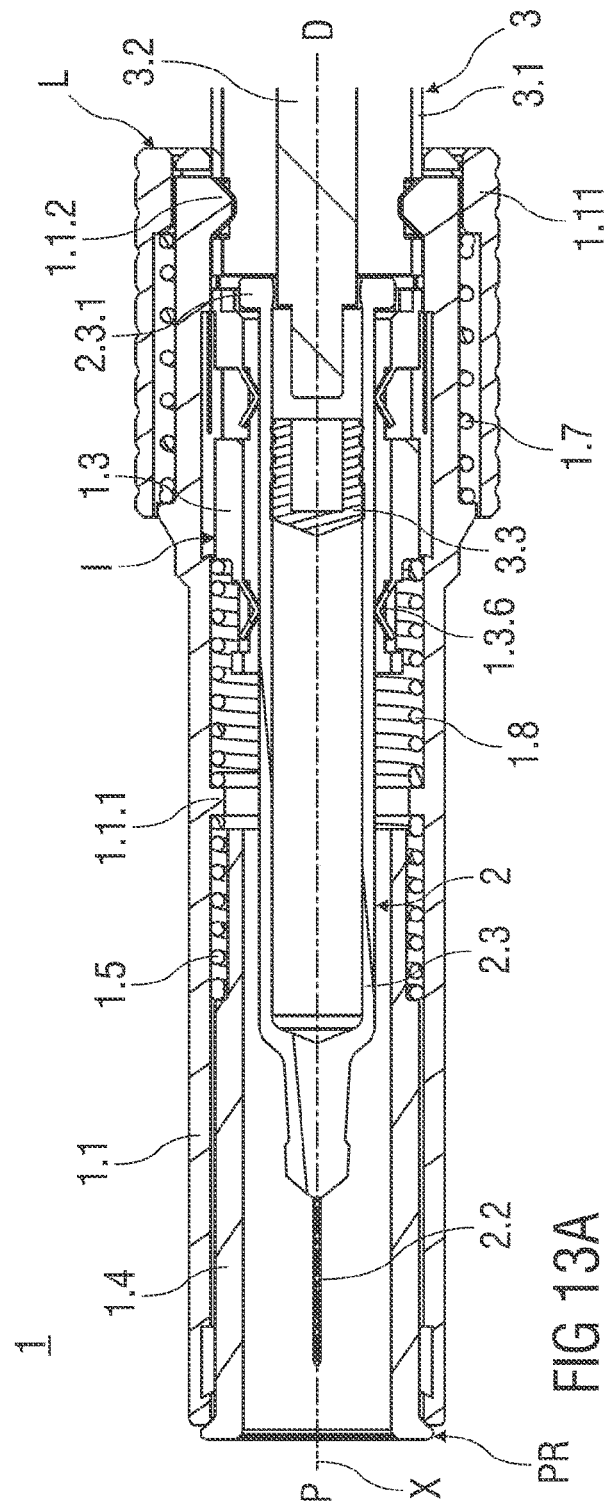
FIGS. 13A and 13B show the front-end device according to the second embodiment of the invention that is connected to the back-end device.
Figure 13B:
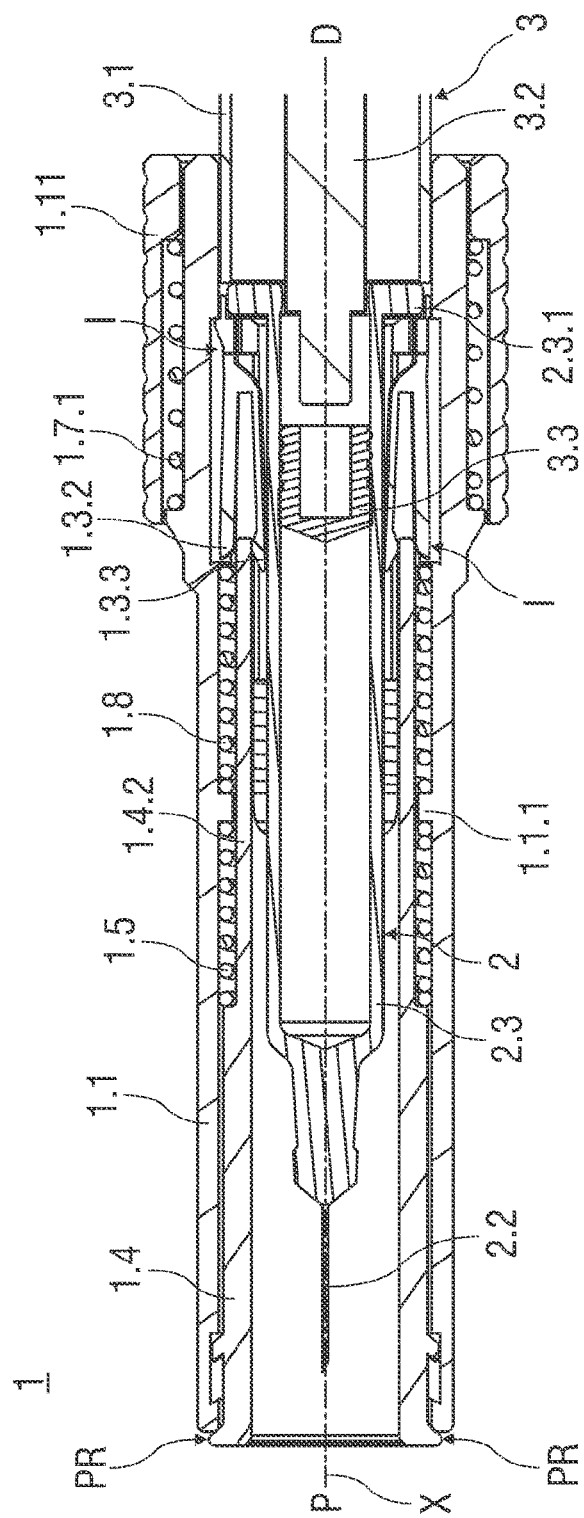

FIGS. 13A and 13B show the front-end device 1 according to the second embodiment of the invention that is connected to the back-end device 3. The tubular cover 2.4 and the needle cap 2.1 has been removed from the pre-filled syringe 2 retained within the front-end device 1 and the injection needle 2.1 is exposed. The front-end device 1 is attached to the back-end device 3 by the latch arms 1.1.2 that latch to a proximal end of a housing 3.1 of the back-end device 3.

The front-end device 1 is attached to or detached from the back-end device 3 by gripping the mounting sleeve 1.11 and axially displacing the mounting sleeve 1.11 with respect to the outer sleeve 1.1 against the biasing force of the mounting sleeve spring 1.7.1 in the proximal direction P to an unlocked position. With the mounting sleeve 1.11 arranged in the unlocked position, the latch arms 1.1.2 are allowed to be deflected in the radial outward direction by the tubular end section of the housing 3.1 pushing against a ramp on the latch arms 1.1.2 upon insertion or removal. The tubular end section of the housing 3.1 may thus be inserted into and/or removed from the open distal end of the front-end device 1 when the mounting collar 1.11 is in the unlocked position. When the tubular end section has been fully inserted the latch arms 1.1.2 are allowed to relax and latch to respective apertures in the tubular end section of the housing 3.1.

When the back-end device 3 is attached to the front-end device 1 the user can release the mounting sleeve 1.11 thus allowing the mounting sleeve spring 1.7.1 to translate the mounting sleeve 1.11 into the locked position. As the tubular end section of the housing 3.1 is inserted into the open distal end of the front-end device 1 the plunger 3.2 is inserted into the barrel 2.3 so as to engage the stopper 3.3 of the syringe 2. The latch arms 1.1.2 latch to the proximal end of the housing 3.1 and attach the front-end device 1 to the back-end device 3. Upon release, the mounting sleeve 1.11 is driven back to the locked position L by the mounting sleeve spring 1.7.1. The mounting sleeve 1.11 in the locked position L abuts against the latch arms 1.1.2 and prevents the latch arms 1.1.2 from deflecting radially outwards thus preventing disengagement of the proximal end of the housing 3.1 from the front end device 1. The auto-injector A is now assembled and ready to be used for an injection delivering the dose of medication to the patient.

The needle shroud 1.4 is pushed against the skin of the patient receiving the injection, whereby the needle shield 1.4 is translated into the outer sleeve 1.1 to a retracted position PR. As best seen in FIG. 13B, the extension arm 1.4.2 engages the release ramp 1.3.3 to deflect the flexible arm 1.3.2 radially inwards, whereby the syringe retainer 1.3 is released from the outer sleeve 1.1 for translation in the proximal direction P. The reusable motor 3.5 of the back-end device 3 may now be activated to translate the syringe retainer 1.3 and the pre-filled syringe 2 in the proximal direction P.

The needle shroud 1.4 may comprise features that communicate to the back-end device 3 that the needle shroud 1.4 is in contact with the skin of the patient. The back-end device 3 may comprise a mechanism like an interlock switch that allows for an expelling of the dose of the medicament contained in the syringe 2 only if the contact of the needle shroud 1.4 with the skin is detected.

Figure 14A:
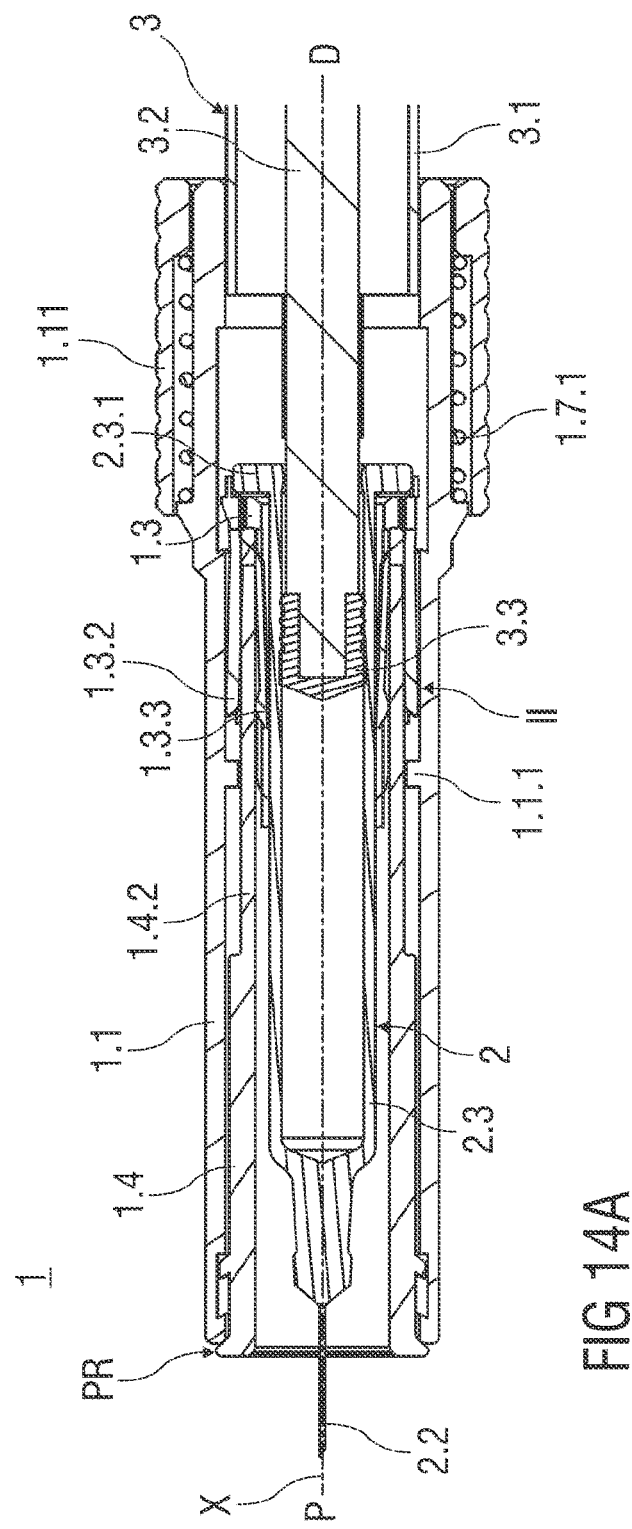
FIGS. 14A and 14B show two sectional views of the front-end device according to the second embodiment in mid injection.
Figure 14B:
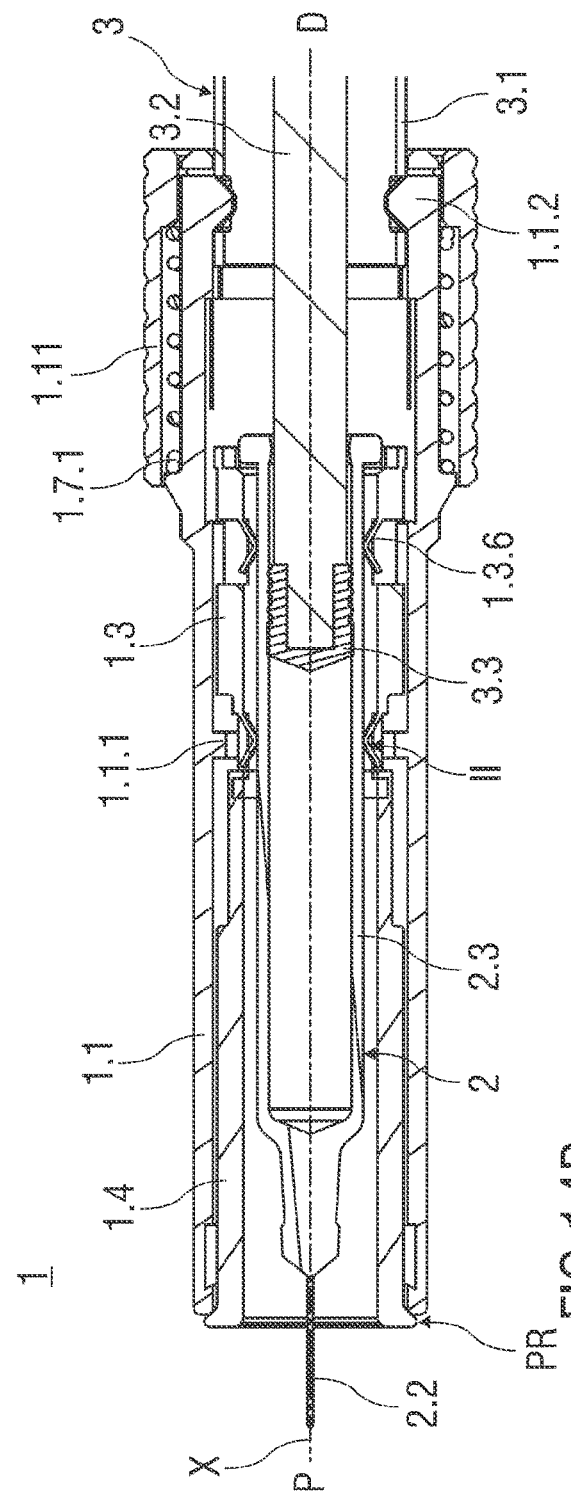

FIGS. 14A and 14B show two sectional views of the front-end device 1 attached to the back end-device 3 in mid injection. The syringe retainer 1.3 holding the syringe 2 is moved proximally to a second position II compressing the return spring 1.8. The injection needle 2.2 protrudes the front-end device 1 in the proximal direction P and is inserted into the skin of the patient. An injection depth may be defined by the length of the compressed return spring 1.8 between the rib 1.1.1 and the syringe retainer 1.3. Alternatively, the needle shroud 1.4 may comprise a stop or rib (not illustrated) that interacts with the syringe retainer 1.4 to limit the penetration depth of the injection needle 2.2.

As the syringe retainer 1.3 has bottomed out the plunger 3.3 connected to the stopper 3.3 is driven by the motor 3.5 of the back-end device 3 in the proximal direction P to expel the dose of the medicament contained in the syringe 2 through the injection needle 2.2.

After the dose of medication is delivered, the auto-injector A is removed from the injection site allowing the needle shroud 1.4 to advance into the advanced position PA driven by the transfer spring 1.5. This motion can be detected by the back-end device 3, which can then release or actively withdraw the plunger 3.2 allowing retraction of the syringe 2. The syringe retainer 1.3 is returned to the first position I by the action of the relaxing return spring 1.8, whereby the injection needle 2.2 is withdrawn from the skin of the patient and covered inside the needle shroud 1.4 for preventing needle access.

Alternatively or additionally, the motor direction of the motor 3.5 is reversed to retract the syringe 2 and the syringe retainer 1.3 to the first position I.

As the transfer spring 1.5 relaxes and moves the needle shroud 1.4 back to the advanced position PA, the extension arm 1.4.2 disengages the release ramp 1.3.3. As the syringe retainer 1.3 is back in the first position I the flexible arm 1.3.2 latches to the outer sleeve 1.1 to re-attach the syringe retainer 1.3 to the outer sleeve 1.1. The auto-injector A is disassembled and the back-end device 3 is detached from the front-end device 1. For this purpose the mounting sleeve 1.11 is gripped and axially displaced with respect to the outer sleeve 1.1 against the biasing force of the mounting sleeve spring 1.7.1 in the proximal direction P to the unlocked position. With the mounting sleeve 1.11 arranged in the unlocked position, the latch arms 1.1.2 are allowed to be deflected in the radial outward direction by the tubular end section of the housing 3.1 pushing against a ramp on the latch arms 1.1.2 when pulled away from the re-usable front end 1. The tubular end section of the housing 3.1 may thus be removed from the open distal end of the front-end device 1 when the mounting collar 1.11 is in the unlocked position. When the tubular end section has been removed the latch arms 1.1.2 are allowed to relax. The mounting sleeve 1.11 returns to the locked position when released. The tubular cover 2.4 holding the needle cap 2.1 is re-inserted into the open proximal end of the front-end device 1, so that the injection needle 2.2 is covered by the needle cap 2.1. The tubular cover 2.4 is pushed into the front-end device 1 to detach the syringe 2 from the syringe retainer 1.3. The empty syringe 2 may then be removed from the front-end device 1 and disposed.

FIGS. 15A and 15B show the assembled auto-injector A comprising the back end-device 3 and the front-end device 1 according to the second embodiment in a perspective and a sectional view. The back-end device 3 and the front-end device 1 are attached to each other by the compression connection means comprising the mounting sleeve 1.11, the mounting sleeve spring 1.7.1 and the latch arms 1.1.2 engaging the proximal end of the housing 3.1.

Although the back-end device 3 in the above described embodiments is motor driven, the above described first and second embodiments of front-end devices 1 may likewise be combined with back-end devices having different thrust means such as a compression spring, a torsion spring, a gas spring or a combustion engine.

The above described back-end device 3 may likewise be combined with a disposable front-end device which is completely discarded after use. Although the re-usable front-end device 1 requires fewer resources and produces less waste, the disposable front-end device avoids the risk of cross contamination since none of its components will get in contact with more than one patient.

The arrangement comprising the locking sleeve 1.6, the clamp arms 1.6.1, the first inward projection 1.2.8 and the clamp spring 1.7 described in the first embodiment of the front-end device 1 is not limited to being used in this embodiment. It may likewise be used for removing and replacing the needle cap 2.1 or protective needle sheath in other re-usable or disposable front-end devices, re-usable or disposable auto-injectors or manually operated injection devices. The locking sleeve 1.6 may be attached to an outer sleeve 1.1 or device cap for joint translation. The connection between the locking sleeve 1.6 and the outer sleeve 1.1 may be arranged to allow relative rotation so as to avoid rotation of the needle cap 2.1 during removal when the outer sleeve 1.1 is rotated. The locking sleeve 1.6 may likewise be arranged to protrude from the device in a manner to allow a user to grip it for removal and replacement. In this case an outer sleeve 1.1 or device cap would not be required.

The invention claimed is:

1. An auto-injector (A) for administering a dose of a liquid medicament, comprising:
a tubular front-end device configured to contain a syringe with an injection needle and a barrel containing the dose of the medicament and comprising a needle shroud configured to rest on skin of a patient receiving an injection; and
a reusable back-end device comprising:
a housing,
a plunger configured to engage a stopper providing a fluid tight seal for a distal end of the barrel,
a motor for displacing the plunger connected to the stopper, wherein the back-end device further comprises an encoder sensor to determine the position of the plunger, wherein the encoder sensor is positioned inside the back-end device,
a gearbox connected to the motor and to the plunger, the gearbox to receive a torque provided by the motor and to transfer the torque to the plunger, wherein the gearbox comprises:
a worm gear attached to the motor, wherein the worm gear receives the torque provided by the motor and rotates in response to receiving the torque in a direction perpendicular to a longitudinal axis of the auto-injector, and
a plurality of gear teeth, wherein a first gear tooth of the plurality of gear teeth is connected to the worm gear, wherein the plurality of gear teeth are configured to receive a rotation of the worm gear and to rotate in a direction parallel to the longitudinal axis of the auto-injector,
wherein the front-end device is attachable to the back-end device, wherein the needle shroud is slidably arranged with respect to the injection needle and wherein an interlock switch is configured to detect an axial position of the needle shroud.

2. The auto-injector (A) according to claim 1, wherein the needle shroud comprises an extension arm that is configured to interact with the interlock switch so as to communicate the axial position of the needle shroud to the back-end device of the auto-injector (A).

3. The auto-injector (A) according to claim 1, wherein the back-end device comprises a sensor unit configured to detect actual parameters of the injection, a memory unit configured to store user related data or specification parameters and a visual, acoustical or haptic feedback provider to the user of the auto-injector (A).

4. The auto-injector (A) according to claim 3, wherein the sensor unit is arranged to measure a current through the motor during needle insertion, wherein the back-end is arranged to compare the measured current to a specified current and to abort the injection when the measured current is out of specification.

5. The auto-injector (A) according to claim 3, wherein the back-end is arranged to detect an initial position of the stopper by the sensor unit and compare it to a specified initial position, wherein the back-end device is arranged to abort the injection when the measured position is more proximal than specified.

6. The auto-injector (A) according to claim 3, wherein the back-end device is arranged to detect a stall of the motor by measuring the current or processing data from the sensor unit and to release or retract the plunger when having detected the stall.

7. The auto-injector (A) according to claim 1, wherein the back-end device is arranged to start an injection cycle when detecting the needle shroud in a retracted position (PR).

8. The auto-injector (A) according to claim 7, wherein the back-end device is arranged to sense the presence of a syringe in the front-end device and to start the injection cycle only when the syringe is present.

9. The auto-injector (A) according to claim 1, wherein the back-end device is arranged to release or to retract the plunger when detecting the needle shroud in an advanced position (PR) after having started the injection cycle.

10. The auto-injector (A) according to claim 1, wherein the back-end device is arranged to detect the position of the stopper by the encoder sensor during an injection cycle in order to adapt the speed of the plunger to different phases of the injection cycle, needle insertion, drug delivery and retraction.

11. The auto-injector (A) according to claim 1, wherein the encoder sensor is arranged as a slotted encoder wheel driven by the motor and arranged between an emitter and a sensor of an optical coupler.

12. The auto-injector (A) of claim 1, further comprising a rack and pinion gear pair, the rack attached to the plunger, the pinion attached to the plurality of teeth, wherein the rack and pinion gear pair is configured to convert a rotation of the plurality of gear teeth into a translation of the plunger along the longitudinal axis.

13. An auto-injector comprising:
   a substantially tubular front-end device; and
   a reusable back-end device attachable to the front-end device, the back-end device comprising:
      a housing,
      a plunger,
      a motor for displacing the plunger,
      an encoder sensor to determine the position of the plunger,
      a gearbox connected to the motor and to the plunger, the gearbox to receive a torque provided by the motor and to transfer the torque to the plunger, wherein the gearbox comprises:
         a worm gear attached to the motor, wherein the worm gear receives the torque provided by the motor and rotates in response to receiving the torque in a direction perpendicular to a longitudinal axis of the auto-injector, and
         a plurality of gear teeth, wherein a first gear tooth of the plurality of gear teeth is connected to the worm gear, wherein the plurality of gear teeth are configured to receive a rotation of the worm gear and to rotate in a direction parallel to the longitudinal axis of the auto-injector.

* * * * *